(12) United States Patent
Mammen et al.

(10) Patent No.: US 7,351,717 B2
(45) Date of Patent: Apr. 1, 2008

(54) SUBSTITUTED PYRROLIDINE AND RELATED COMPOUNDS

(75) Inventors: Mathai Mammen, Redwood Shores, CA (US); Adam Hughes, San Francisco, CA (US); Yu-hua Ji, Redwood City, CA (US); Li Li, Sunnyvale, CA (US); Weijiang Zhang, Cupertino, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 11/602,703

(22) Filed: Nov. 21, 2006

(65) Prior Publication Data

US 2007/0135482 A1   Jun. 14, 2007

Related U.S. Application Data

(63) Continuation of application No. 10/865,527, filed on Jun. 10, 2004, now Pat. No. 7,183,292.

(60) Provisional application No. 60/478,456, filed on Jun. 13, 2003.

(51) Int. Cl.
*A61K 31/445* (2006.01)
*A61K 31/40* (2006.01)
*C07D 207/04* (2006.01)
*C07D 211/06* (2006.01)

(52) U.S. Cl. ............... 514/315; 546/184; 546/246; 546/247; 548/566; 548/567; 548/568; 514/428

(58) Field of Classification Search ............... 546/184, 546/246, 247; 548/566, 567, 568; 514/315, 514/428
See application file for complete search history.

(56) References Cited

U.S. PATENT DOCUMENTS

| | | | |
|---|---|---|---|
| 3,192,206 A | 6/1965 | Lunsford et al. |
| 3,192,210 A | 6/1965 | Lunsford et al. |
| 3,192,221 A | 6/1965 | Lunsford et al. |
| 3,247,222 A | 4/1966 | Lunsford |
| 3,732,247 A | 5/1973 | Helsley et al. |
| 3,984,557 A | 10/1976 | Welstead, Jr. |
| 4,002,766 A | 1/1977 | Welstead, Jr. |
| 4,594,343 A | 6/1986 | Shanklin, Jr. |
| 4,810,713 A | 3/1989 | Yanni et al. |
| 4,950,674 A | 8/1990 | Yanni et al. |
| 5,070,087 A | 12/1991 | Teng et al. |
| 5,096,890 A | 3/1992 | Cross et al. |
| 5,233,053 A | 8/1993 | Cross et al. |
| 5,340,831 A | 8/1994 | Cross et al. |
| 5,344,835 A | 9/1994 | Alker et al. |
| 5,486,527 A | 1/1996 | Alker et al. |
| 5,607,950 A | 3/1997 | Alker et al. |
| 5,750,540 A | 5/1998 | Tsuchiya et al. |
| 5,932,594 A | 8/1999 | Cross et al. |
| 6,130,232 A | 10/2000 | Mase et al. |
| 6,403,810 B2 | 6/2002 | Klaus et al. |
| 6,433,027 B1 | 8/2002 | Bozung et al. |
| 6,693,202 B1 | 2/2004 | Aggen et al. |
| 2003/0018019 A1 | 1/2003 | Meade et al. |
| 2004/0122014 A1 | 6/2004 | Mammen et al. |
| 2005/0026954 A1 | 2/2005 | Mammen et al. |
| 2005/0113413 A1 | 5/2005 | Wilson et al. |

FOREIGN PATENT DOCUMENTS

| | | |
|---|---|---|
| EP | 0 178 946 A2 | 4/1986 |
| EP | 0 178 947 A2 | 4/1986 |
| EP | 0 235 463 A2 | 9/1987 |
| EP | 0 388 054 A1 | 9/1990 |
| EP | 0 999 205 A1 | 5/2000 |
| EP | 1 020 499 A1 | 7/2000 |
| JP | 4-90559 | 3/1992 |
| JP | 4-151168 | 5/1992 |
| JP | 11 100366 | 4/1999 |

(Continued)

OTHER PUBLICATIONS

Broadley et al., "Muscarinic Receptor Agonists and Antagonists", Molecules, 6, pp. 142-193 (2001).
Cale et al., "A Series of Central Nervous System Stimulants Based on the 4-Substituted 3,3-Diphenyl-2-pyrrolidinone Skeleton. II", J. Med. Chem., 10(2), pp. 214-222 (1967).
Eglen et al., "Muscarinic Receptor Subtypes:Pharmacology and Therapeutic Potentisl", DN&P, 10(8), pp. 462-469 (1997).
Graul et al., "Darifenacin", Drugs of the Future, 21(11), pp. 1105-1108 (1996).
Taniguchi et al., "Agents for the Treatment of Overactive Detrusor, VI. ¹ᵃ⁾ Synthesis and Pharmacological Properties of Acetamide Derivatives Bearing Cyclic Amines in N-Substitutents", Chem. Pharm. Bull, 42(1), pp. 74-84) 1994.

(Continued)

*Primary Examiner*—Golam M. M. Shameem
(74) *Attorney, Agent, or Firm*—Jeffrey A. Hagenah; Shelley Eberle

(57) ABSTRACT

This invention is directed to compounds of formula I:

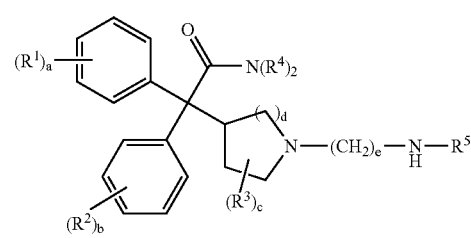

wherein $R^1$-$R^5$ and a-e are as defined in the specification; or pharmaceutically-acceptable salt or solvate or stereoisomer thereof. The invention also directed to pharmaceutical compositions containing such compounds; processes and intermediates useful for preparing such compounds; and methods for treating disease conditions mediated by muscarinic receptors using such compounds.

31 Claims, No Drawings

FOREIGN PATENT DOCUMENTS

| | | |
|---|---|---|
| WO | WO 91/09013 A1 | 6/1991 |
| WO | WO 98/54167 A1 | 12/1998 |
| WO | WO 99/64043 A1 | 12/1999 |
| WO | WO 2004/041806 A2 | 5/2004 |
| WO | WO 2004/089892 A2 | 10/2004 |

OTHER PUBLICATIONS

Zlotos et al., "Muscarinic receptor agonists and antagonists", Exp. Opin. Ther. Patents, 9(8), pp. 1029-1053 (1999).

Yeh, et al., "Molecular and Structural Basis of Resting and Use-Dependent Block of Sodium Current Defined Using Disopyramide Analogues", Biophys. J., vol. 51, pp. 123-135 (1987).

US 7,351,717 B2

SUBSTITUTED PYRROLIDINE AND RELATED COMPOUNDS

CROSS-REFERENCE TO RELATED APPLICATIONS

This application is a continuation application of U.S. Ser. No. 10/865,527, filed Jun. 10, 2004, now U.S. Pat. No. 7,183,292, which claims the benefit of U.S. Provisional Application No. 60/478,456, filed on Jun. 13, 2003; the entire disclosures of which are incorporated herein by reference in their entirety.

BACKGROUND OF THE INVENTION

1. Field of the Invention

This invention is directed to substituted pyrrolidine and related compounds having muscarinic receptor antagonist or anticholinergic activity. This invention is also directed to pharmaceutical compositions comprising such compounds; methods of using such compounds to treat medical conditions mediated by muscarinic receptors; and processes and intermediates useful for preparing such compounds.

2. State of the Art

Pulmonary disorders, such as chronic obstructive pulmonary disease (COPD) and asthma, afflict many millions of people worldwide and such disorders are a leading cause of morbidity and mortality.

Muscarinic receptor antagonists are known to provide bronchoprotective effects and therefore, such compounds are useful for treating respiratory disorders, such as COPD and asthma. When used to treat such disorders, muscarinic receptor antagonists are typically administered by inhalation. However, even when administered by inhalation, a significant amount of the muscarinic receptor antagonist is often absorbed into the systemic circulation resulting in systemic side effects, such as dry mouth, urinary retention, mydriasis and cardiovascular side effects.

Additionally, many inhaled muscarinic receptor antagonists have a relatively short duration of action requiring that they be administered several times per day. Such a multiple-daily dosing regime is not only inconvenient but also creates a significant risk of inadequate treatment due to patient non-compliance with the required frequent dosing schedule.

Accordingly, a need exists for new muscarinic receptor antagonists. In particular, a need exists for new muscarinic receptor antagonists having high potency and reduced systemic side effects when administered by inhalation. Additionally, a need exists for inhaled muscarinic receptor antagonists having a long duration of action thereby allowing for once-daily or even once-weekly dosing. Such compounds are expected to be particularly effective for treating pulmonary disorders, such as COPD and asthma, while reducing or eliminating side effects, such as dry-mouth.

SUMMARY OF THE INVENTION

The present invention provides novel substituted pyrrolidine and related compounds which have muscarinic receptor antagonist or anticholinergic activity. Among other properties, compounds of this invention have been found to possess a surprising and unexpected binding affinity for $hM_2$ and $hM_3$ muscarinic receptor subtypes compared to related compounds. Additionally, compounds of this invention have been found to have surprising and unexpected lung selectivity when administered by inhalation thereby resulting in reduced systemic side effects. Moreover, compounds of this invention have been found to possess a surprising and unexpectedly duration of bronchoprotection when administered by inhalation.

Accordingly, in one of its composition aspects, this invention provides a compound of formula I:

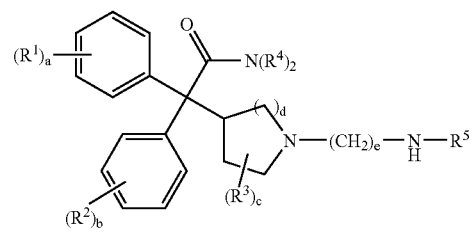

wherein
each $R^1$ and $R^2$ is independently selected from $C_{1-4}$ alkyl, $C_{2-4}$ alkenyl, $C_{2-4}$ alkynyl, $C_{3-6}$ cycloalkyl, cyano, halo, —$OR^a$, —$SR^a$, —$S(O)R^a$, —$S(O)_2R^a$ and —$NR^bR^c$; or two adjacent $R^1$ groups or two adjacent $R^2$ groups are joined to form $C_{3-6}$ alkylene, —($C_{2-4}$ alkylene)-O— or —O—($C_{1-4}$ alkylene)-O—;
each $R^3$ is independently selected from $C_{1-4}$ alkyl and fluoro;
each $R^4$ is independently selected from hydrogen, $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl, $C_{3-6}$ heterocyclic, —$CH_2$—$R^6$ and —$CH_2CH_2$—$R^7$; or both $R^4$ groups are joined together with the nitrogen atom to which they are attached to form $C_{3-6}$ heterocyclic;
$R^5$ is selected from $C_{1-6}$ alkyl, $C_{2-6}$ alkenyl, $C_{2-6}$ alkynyl, $C_{3-6}$ cycloalkyl, and —$CH_2$—$R^8$; wherein each alkyl, alkenyl and alkynyl group is optionally substituted with —OH or 1 to 5 fluoro substituents;
each $R^6$ is independently selected from $C_{3-6}$ cycloalkyl, $C_{6-10}$ aryl, $C_{2-9}$ heteroaryl and $C_{3-6}$ heterocyclic;
each $R^7$ is independently selected from $C_{3-6}$ cycloalkyl, $C_{6-10}$ aryl, $C_{2-9}$ heteroaryl, $C_{3-6}$ heterocyclic, —OH, —O($C_{1-6}$ alkyl), —O($C_{3-6}$ cycloalkyl), —O($C_{6-10}$ aryl), —O($C_{2-9}$ heteroaryl), —S($C_{1-6}$ alkyl), —S(O)($C_{1-6}$ alkyl), —S(O)$_2$($C_{1-6}$ alkyl), —S($C_{3-6}$ cycloalkyl), —S(O)($C_{3-6}$ cycloalkyl), —S(O)$_2$($C_{3-6}$ cycloalkyl), —S($C_{6-10}$ aryl), —S(O)($C_{6-10}$ aryl), —S(O)$_2$($C_{6-10}$ aryl), —S($C_{2-9}$ heteroaryl), —S(O)($C_{2-9}$ heteroaryl) and —S(O)$_2$($C_{2-9}$ heteroaryl);
each $R^8$ is independently selected from $C_{3-6}$ cycloalkyl, $C_{6-10}$ aryl, $C_{2-9}$ heteroaryl and $C_{3-6}$ heterocyclic;
each $R^a$ is independently selected from hydrogen, $C_{1-4}$ alkyl, $C_{2-4}$ alkenyl, $C_{2-4}$ alkynyl and $C_{3-6}$ cycloalkyl;
each $R^b$ and $R^c$ is independently selected from hydrogen, $C_{1-4}$ alkyl, $C_{2-4}$ alkenyl, $C_{2-4}$ alkynyl and $C_{3-6}$ cycloalkyl; or $R^b$ and $R^c$ are joined together with the nitrogen atom to which they are attached to form $C_{3-6}$ heterocyclic;
a is an integer from 0 to 3;
b is an integer from 0 to 3;
c is an integer from 0 to 4;
d is 1 or 2;
e is 8 or 9;
wherein each alkyl, alkylene, alkenyl, alkynyl and cycloalkyl group in $R^1$, $R^2$, $R^3$, $R^4$, $R^7$, $R^a$, $R^b$ and $R^c$ is optionally substituted with 1 to 5 fluoro substituents; each aryl, cycloalkyl, heteroaryl and heterocyclic group in $R^1$, $R^2$, $R^4$, $R^5$, $R^6$, $R^7$, $R^8$, $R^a$, $R^b$ and $R^c$ is optionally substituted with 1 to 3 substituents independently selected from $C_{1-4}$ alkyl, $C_{2-4}$ alkenyl, $C_{2-4}$ alkynyl, cyano, halo, —O($C_{1-4}$ alkyl), —S($C_{1-4}$ alkyl), —S(O)($C_{1-4}$ alkyl), —S(O)$_2$($C_{1-4}$ alkyl),—NH$_2$, —NH($C_{1-4}$ alkyl) and —N($C_{1-4}$ alkyl)$_2$, wherein each alkyl, alkylene, alkenyl and alkynyl group is optionally substituted with 1 to 5 fluoro substituents; and each —CH$_2$— group in —(CH$_2$)$_e$— is optionally substituted with 1 or 2 substituents independently selected from $C_{1-2}$ alkyl,—OH and fluoro;

or a pharmaceutically-acceptable salt or solvate or stereoisomer thereof.

In another of its composition aspects, this invention provides a compound of formula II:

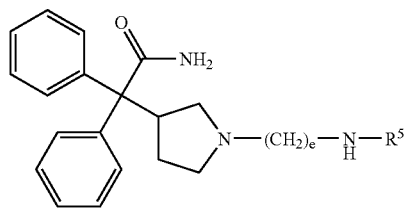

II wherein $R^5$ and e are as defined herein; or a pharmaceutically-acceptable salt or solvate or stereoisomer thereof.

In separate and distinct embodiments, this invention is also directed to compounds of formula II wherein the stereochemistry at the 3-position of the pyrrolidine ring has the (R) configuration; and compounds of formula II wherein the stereochemistry at the 3-position of the pyrrolidine ring has the (S) configuration.

In another of its composition aspects, this invention provides a pharmaceutical composition comprising a pharmaceutically-acceptable carrier and a therapeutically effective amount of a compound of formula I, or a pharmaceutically-acceptable salt or solvate or stereoisomer thereof. Such pharmaceutical compositions may optionally contain other therapeutic agents. Accordingly, in one embodiment, this invention is directed to such a pharmaceutical composition wherein the composition further comprises a therapeutically effective amount of a steroidal anti-inflammatory agent, such as a corticosteroid; a β$_2$ adrenergic receptor agonist; a phosphodiesterase-4 inhibitor; or a combination thereof.

The compounds of this invention are muscarinic receptor antagonists. Accordingly, in one of its method aspects, this invention provides a method for treating a mammal having a medical condition which is alleviated by treatment with a muscarinic receptor antagonist, the method comprising administering to the mammal a therapeutically effective amount of a compound of formula I, or a pharmaceutically-acceptable salt or solvate or stereoisomer thereof.

In another of its method aspects, this invention provides a method for treating a pulmonary disorder, the method comprising administering to a patient in need of treatment a therapeutically effective amount of a compound of formula I, or a pharmaceutically-acceptable salt or solvate or stereoisomer thereof.

In yet another of its method aspects, this invention provides a method of producing bronchodilation in a patient, the method comprising administering by inhalation to the patient a bronchodilation-producing amount of a compound of formula I, or a pharmaceutically-acceptable salt or solvate or stereoisomer thereof.

In still another of its method aspects, this invention provides a method for treating chronic obstructive pulmonary disease or asthma, the method comprising administering to a patient in need of treatment a therapeutically effective amount of a compound of formula I or a pharmaceutically-acceptable salt or solvate or stereoisomer thereof.

Since compounds of this invention possess muscarinic receptor antagonist activity, such compounds are also useful as research tools for studying biological systems or samples having a muscarinic receptor or for studying the activity of other chemical compounds. Accordingly, in yet another of its method aspects, this invention provides a method for using a compound of formula I or a pharmaceutically acceptable salt or solvate or stereoisomer thereof as a research tool for studying a biological system or sample, or for discovering new chemical compounds having muscarinic receptor antagonist activity.

This invention is also directed to processes and novel intermediates useful for preparing compounds of formula I or a salt or solvate or stereoisomer thereof. Accordingly, in another of its method aspects, this invention provides a process of preparing a compound of formula I, the process comprising:

(a) reacting a compound of formula III with a compound of formula IV in the presence of a reducing agent;

(b) reacting a compound of formula V with a compound of formula VI in the presence of a reducing agent;

(c) reacting a compound of formula VII with a compound of formula IV; or (d) reacting a compound of formula V with a compound of formula VIII; and then (e) removing any protecting groups to provide a compound of formula I or a salt thereof; wherein the compounds of formulae I and III-VIII are as defined herein.

In one embodiment, the above process further comprises the additional step of forming a pharmaceutically-acceptable salt of a compound of formula I.

In another of its method aspects, this invention provides a process for preparing a pharmaceutically-acceptable salt of a compound of formula I, the process comprising contacting a compound of formula IX:

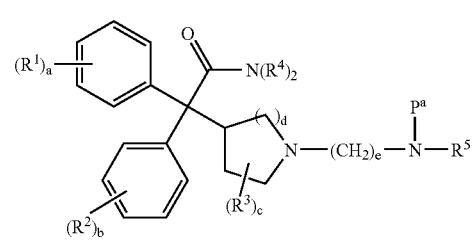

IX wherein $R^1$-$R^5$ and a-e are as defined herein; and $P^a$ is an acid-labile amino-protecting group; with a pharmaceutically-acceptable acid to form a pharmaceutically-acceptable salt of a compound of formula I.

In other embodiments, this invention is directed to the other processes described herein; and to the product prepared by any of the processes described herein.

In another of its composition aspects, this invention provides a compound of formula X:

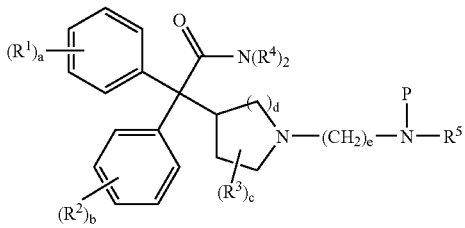

wherein $R^1$-$R^5$ and a-e are as defined herein; and P is an amino-protecting group; or a salt or solvate or stereoisomer thereof; for use as an intermediate for preparing compounds of formula I.

In another of its composition aspects, this invention provides a compound of formula XI:

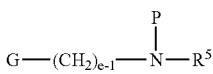

XI wherein $R^5$ and e are as defined herein; P is an amino-protecting group; and G is selected from —CHO, —CH(OR$^f$)$_2$, —CH$_2$OH and —CH$_2$-L, wherein each R$^f$ is independently C$_{1-6}$ alkyl or both R$^f$ groups are joined to form C$_{2-6}$ alkylene; and L is a leaving group; or a salt or stereoisomer thereof; for use as an intermediate for preparing compounds of formula I; provided that when L is chloro, P is not ethoxycarbonyl (i.e., CH$_3$CH$_2$OC(O)—).

In additional separate and distinct aspects, this invention provides:

a compound of formula I, or a pharmaceutically-acceptable salt or solvate or stereoisomer thereof, for use in therapy;

a compound of formula I, or a pharmaceutically-acceptable salt or solvate or stereoisomer thereof, for use as a medicament;

a compound of formula I, or a pharmaceutically-acceptable salt or solvate or stereoisomer thereof, for use in treating a pulmonary disorder, including chronic obstructive pulmonary disease and asthma;

a medicament containing a compound of formula I, or a pharmaceutically-acceptable salt or solvate or stereoisomer thereof;

use of a compound of formula I, or a pharmaceutically-acceptable salt or solvate or stereoisomer thereof, for treatment of a pulmonary disorder, including chronic obstructive pulmonary disease and asthma;

use of a compound of formula I, or a pharmaceutically-acceptable salt or solvate or stereoisomer thereof, as a medicament for the treatment of a pulmonary disorder, including chronic obstructive pulmonary disease and asthma;

use of a compound of formula I, or a pharmaceutically-acceptable salt or solvate or stereoisomer thereof, for manufacture of a medicament; and use of a compound of formula I, or a pharmaceutically-acceptable salt or solvate or stereoisomer thereof, for manufacture of a medicament for treatment of a pulmonary disorder, including chronic obstructive pulmonary disease and asthma.

DETAILED DESCRIPTION OF THE INVENTION

This invention provides novel substituted pyrrolidine and related compounds of formula I, or pharmaceutically-acceptable salts or solvates or stereoisomers thereof. These compounds may contain one or more chiral centers and, when such a chiral center or centers are present, this invention is directed to racemic mixtures; pure stereoisomers (i.e., individual enantiomers or diastereomers); and stereoisomer-enriched mixtures of such isomers, unless otherwise indicated. When a particular stereoisomer is shown, it will be understood by those skilled in the art that minor amounts of other stereoisomers may be present in the compositions of this invention unless otherwise indicated, provided that the utility of the composition as a whole is not eliminated by the presence of such other isomers.

The compounds of this invention also contain several basic groups (e.g., amino groups) and therefore, the compounds of formula I can exist as the free base or in various salt forms. All such forms are included within the scope of this invention. Also included within the scope of this invention are pharmaceutically-acceptable solvates of the compounds of formula I or the salts thereof.

Additionally, where applicable, all cis-trans or E/Z isomers (geometric isomers), tautomeric forms and topoisomeric forms of the compounds of formula I are included within the scope of this invention unless otherwise specified.

The nomenclature used herein to name the compounds of this invention is illustrated in the Examples herein. Generally, this nomenclature has been derived using the commercially-available AutoNom software (MDL, San Leandro, Calif.).

REPRESENTATIVE EMBODIMENTS

The following substituents and values are intended to provide representative examples and embodiments of various aspects of this invention. These representative values are intended to further define such aspects and embodiments and are not intended to exclude other embodiments or limit the scope of this invention. In this regard, the representation herein that a particular value or substituent is preferred is not intended in any way to exclude other values or substituents from this invention unless specifically indicated.

In a specific embodiment, $R^1$ or $R^2$, when present, are independently selected from C$_{1-4}$ alkyl, fluoro, chloro and —OR$^a$; wherein each alkyl group is optionally substituted with 1 to 3 fluoro substituents. In another specific embodiment, each $R^1$ and $R^2$ is C$_{1-2}$ alkyl or fluoro. Representative $R^1$ and $R^2$ groups include, but are not limited to, methyl, ethyl, n-propyl, isopropyl, difluoromethyl, trifluoromethyl, 2,2,2-trifluoroethyl, fluoro, chloro, methoxy, ethoxy, difluoromethoxy and trifluoromethoxy.

In a specific embodiment, each $R^3$, when present, is independently selected from C$_{1-2}$ alkyl and fluoro; wherein each alkyl group is optionally substituted with 1 to 3 fluoro substituent. When two $R^3$ substituents are present, they can be on the same or different carbon atoms. Representative $R^3$ groups include, but are not limited to, methyl, ethyl, difluoromethyl, trifluoromethyl and fluoro.

In specific embodiments, each $R^4$ is independently hydrogen or C$_{1-4}$ alkyl; or each $R^4$ is independently hydrogen or C$_{1-2}$ alkyl; or each $R^4$ is hydrogen. Representative $R^4$ groups include, but are not limited to, hydrogen, methyl and ethyl.

Alternatively, in another specific embodiment, both $R^4$ groups are joined together with the nitrogen atom to which they are attached to form a $C_{3-5}$ heterocyclic ring optionally containing one additional heteroatom selected from nitrogen, oxygen or sulfur. Representative heterocyclic rings include, but are not limited to, pyrrolidin-1-yl, piperidin-1-yl, piperazin-1-yl, morpholin-4-yl and thiomorpholin-4-yl.

In specific embodiments, $R^5$ is $C_{1-5}$ alkyl; or $R^5$ is $C_{1-4}$ alkyl; or $R^5$ is $C_{1-3}$ alkyl; or $R^5$ is $C_{1-2}$ alkyl; wherein the alkyl group is optionally substituted with —OH or 1 to 3 fluoro substituents. Representative $R^5$ groups in this embodiment include, but are not limited to, methyl, ethyl, 2-hydroxyethyl, 2,2,2-trifluoroethyl, n-propyl, isopropyl, 1-hydroxyprop-2-yl, n-butyl and isobutyl. In one embodiment, $R^5$ is methyl.

In other specific embodiments, $R^5$ is $C_{3-5}$ cycloalkyl; or $R^5$ is $C_{3-4}$ cycloalkyl; wherein the cycloalkyl group is optionally substituted with —OH or 1 to 3 fluoro substituents. Representative $R^5$ groups in this embodiment include, but are not limited to, cyclopropyl, cyclobutyl and cyclopentyl.

In another specific embodiment, $R^5$ is —CH$_2$—$R^8$, wherein $R^8$ is as defined herein. In separate aspects of this embodiment, $R^5$ (i.e., —CH$_2$—$R^8$) is selected from:

(a) —CH$_2$—(C$_{3-5}$ cycloalkyl); or —CH$_2$—(C$_{3-4}$ cycloalkyl); wherein the cycloalkyl group is optionally substituted with —OH or 1 to 3 fluoro substituents;

(b) —CH$_2$-(phenyl), i.e., benzyl, wherein the phenyl group is optionally substituted with 1 to 3 substituents independently selected from $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substituent.

Representative $R^5$ groups in this embodiment include, but are not limited to, cyclopropylmethyl, cyclobutylmethyl and cyclopentylmethyl; and benzyl, 4-cyanobenzyl, 3-methylbenzyl, 4-methylbenzyl, 4-trifluoromethoxybenzyl, 3-fluorobenzyl and 4-fluorobenzyl.

In a specific embodiment, each $R^6$ is independently phenyl; wherein each phenyl group is optionally substituted with 1 to 3 substituents independently selected from $C_{1-4}$ alkyl, cyano, fluoro, chloro, —O($C_{1-4}$ alkyl), —S($C_{1-4}$ alkyl) and —S(O)$_2$($C_{14}$ alkyl); where each alkyl group is optionally substituted with 1 to 3 fluoro substituent.

In a specific embodiment, each $R^7$ is independently selected from phenyl, —OH and —O($C_{1-2}$ alkyl); wherein each alkyl group is optionally substituted with 1 to 3 fluoro substituent; and each phenyl group is optionally substituted with 1 to 3 substituents independently selected from $C_{1-4}$ alkyl, cyano, fluoro, chloro, —O($C_{1-4}$ alkyl), —S($C_{1-4}$ alkyl) and —S(O)$_2$($C_{14}$ alkyl); where each alkyl group is optionally substituted with 1 to 3 fluoro substituent.

In specific embodiments, each $R^a$ is independently selected from hydrogen and $C_{1-3}$ alkyl; or hydrogen and $C_{1-2}$ alkyl; wherein each alkyl group is optionally substituted with 1 to 3 fluoro substituent. Representative $R^a$ groups include, but are not limited to, methyl, ethyl, n-propyl, isopropyl, difluoromethyl, trifluoromethyl and 2,2,2-trifluoroethyl.

In specific embodiments, each $R^b$ and $R^c$ is independently selected from hydrogen and $C_{1-3}$ alkyl; or hydrogen and $C_{1-2}$ alkyl; wherein each alkyl group is optionally substituted with 1 to 3 fluoro substituent. Representative $R^b$ and $R^c$ groups include, but are not limited to, methyl, ethyl, n-propyl, isopropyl, difluoromethyl, trifluoromethyl and 2,2,2-trifluoroethyl.

Alternatively, in another specific embodiment, $R^b$ and $R^c$ are joined together with the nitrogen atom to which they are attached to form a $C_{3-5}$ heterocyclic ring optionally containing one additional heteroatom selected from nitrogen, oxygen or sulfur. Representative heterocyclic rings include, but are not limited to, pyrrolidin-1-yl, piperidin-1-yl, piperazin-1-yl, morpholin-4-yl and thiomorpholin-4-yl.

In specific embodiments, a is 0, 1 or 2; or a is 0 or 1; or a is 0.

In specific embodiments, b is 0, 1 or 2; or b is 0 or 1; or b is 0.

In specific embodiments, c is 0, 1 or 2; or c is 0 or 1; or c is 0.

When d is 1, i.e., when the ring defined by d is a pyrrolidine ring, then in one embodiment, the stereocenter at the 3-position of the pyrrolidine ring (i.e., the carbon atom bearing the 1-carbamoyl-1,1-diphenylmethyl group) has the (S) stereochemistry. In another embodiment, this stereocenter has the (R) stereochemistry.

In one embodiment, e is 8. In another embodiment, e is 9.

A particular embodiment of the present invention are compounds of formula I wherein both $R^4$ groups are hydrogen, a, b and c are 0; d is 1; e is 8 or 9; and $R^5$ is $C_{1-3}$ alkyl; or $C_{1-2}$ alkyl; or a pharmaceutically-acceptable salt or solvate or stereoisomer thereof.

Another particular embodiment of the present invention are compounds of formula I wherein both $R^4$ groups are hydrogen, a, b and c are 0; d is 1; e is 8 or 9; and $R^5$ is $C_{3-5}$ cycloalkyl; or $C_{3-4}$ cycloalkyl; or a pharmaceutically-acceptable salt or solvate or stereoisomer thereof.

Yet another particular embodiment of the present invention are compounds of formula I wherein $R^5$ is methyl; and $R^1$, $R^2$, $R^3$, $R^4$, a, b, c, d, and e are as defined herein; or a pharmaceutically-acceptable salt or solvate or stereoisomer thereof.

Other specific embodiments of the present invention are compounds of formula IIa:

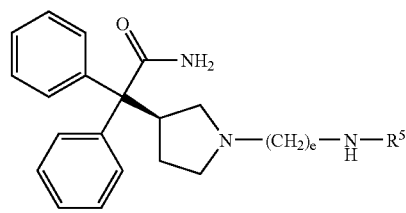

IIa wherein $R^5$ and e are as defined in Table I, or a pharmaceutically-acceptable salt or solvate thereof.

TABLE I

| Example No. | $R^5$ | e |
|---|---|---|
| 1 | —CH$_3$ | 8 |
| 2 | —CH(CH$_3$)$_2$ | 8 |
| 3 | —CH$_2$CH$_2$CH$_3$ | 8 |
| 4 | -cyclopropyl | 8 |
| 5 | -cyclobutyl | 8 |
| 6 | -cyclopentyl | 8 |
| 7 | —CH$_2$CH$_3$ | 8 |
| 8 | —CH$_2$CH$_2$OH | 8 |
| 9 | —CH(CH$_3$)CH$_2$OH (R)-isomer | 8 |
| 10 | —CH(CH$_3$)CH$_2$OH | 8 |
| 11 | —CH(CH$_3$)CH$_2$OH (S)-isomer | 8 |
| 12 | —CH$_2$CF$_3$ | 8 |
| 13 | —CH$_2$Ph† | 8 |
| 14 | —CH$_3$ | 9 |
| 15 | —CH(CH$_3$)$_2$ | 9 |
| 16 | —CH$_2$CH$_2$CH$_3$ | 9 |
| 17 | -cyclopropyl | 9 |

TABLE I-continued

| Example No. | R⁵ | e |
|---|---|---|
| 18 | -cyclobutyl | 9 |
| 19 | -cyclopentyl | 9 |
| 20 | —CH₂CH₃ | 9 |
| 21 | —CH₂CH₂OH | 9 |
| 22 | —CH(CH₃)CH₂OH (R)-isomer | 9 |
| 23 | —CH(CH₃)CH₂OH | 9 |
| 24 | —CH(CH₃)CH₂OH (S)-isomer | 9 |
| 25 | —CH₂CF₃ | 9 |
| 26 | —CH₂Ph | 9 |

†Ph = phenyl.

Still other specific embodiments of the present invention are compounds of formula IIb:

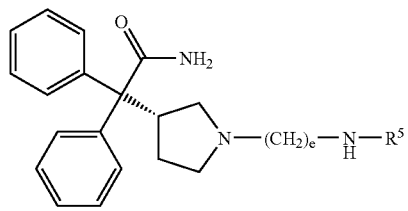

IIb wherein R⁵ and e are as defined in Table II, or a pharmaceutically-acceptable salt or solvate thereof.

TABLE II

| Example No. | R⁵ | e |
|---|---|---|
| 27 | —CH₃ | 8 |
| 28 | —CH(CH₃)₂ | 8 |
| 29 | —CH₂CH₂CH₃ | 8 |
| 30 | -cyclopropyl | 8 |
| 31 | -cyclobutyl | 8 |
| 32 | -cyclopentyl | 8 |
| 33 | —CH₂CH₃ | 8 |
| 34 | —CH₂CH₂OH | 8 |
| 35 | —CH(CH₃)CH₂OH (R)-isomer | 8 |
| 36 | —CH(CH₃)CH₂OH | 8 |
| 37 | —CH(CH₃)CH₂OH (S)-isomer | 8 |
| 38 | —CH₂CF₃ | 8 |
| 39 | —CH₂Ph† | 8 |
| 40 | —CH₃ | 9 |
| 41 | —CH(CH₃)₂ | 9 |
| 42 | —CH₂CH₂CH₃ | 9 |
| 43 | -cyclopropyl | 9 |
| 44 | -cyclobutyl | 9 |
| 45 | -cyclopentyl | 9 |
| 46 | —CH₂CH₃ | 9 |
| 47 | —CH₂CH₂OH | 9 |
| 48 | —CH(CH₃)CH₂OH (R)-isomer | 9 |
| 49 | —CH(CH₃)CH₂OH | 9 |
| 50 | —CH(CH₃)CH₂OH (S)-isomer | 9 |
| 51 | —CH₂CF₃ | 9 |
| 52 | —CH₂Ph | 9 |

†Ph = phenyl.

Still other specific embodiments of the present invention are compounds of formula XII:

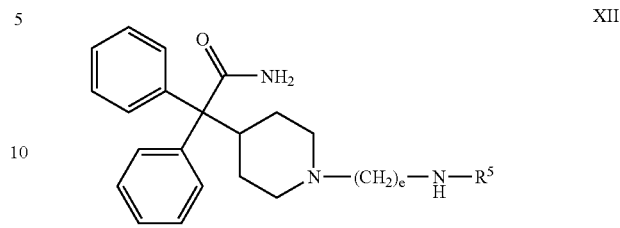

XII wherein R⁵ and e are as defined in Table III, or a pharmaceutically-acceptable salt or solvate thereof.

TABLE III

| Example No. | R⁵ | e |
|---|---|---|
| 53 | —CH₃ | 8 |
| 54 | —CH(CH₃)₂ | 8 |
| 55 | —CH₂CH₂CH₃ | 8 |
| 56 | -cyclopropyl | 8 |
| 57 | -cyclobutyl | 8 |
| 58 | -cyclopentyl | 8 |
| 59 | —CH₂CH₃ | 8 |
| 60 | —CH₂CH₂OH | 8 |
| 61 | —CH(CH₃)CH₂OH (R)-isomer | 8 |
| 62 | —CH(CH₃)CH₂OH | 8 |
| 63 | —CH(CH₃)CH₂OH (S)-isomer | 8 |
| 64 | —CH₂CF₃ | 8 |
| 65 | —CH₂Ph† | 8 |
| 66 | —CH₃ | 9 |
| 67 | —CH(CH₃)₂ | 9 |
| 68 | —CH₂CH₂CH₃ | 9 |
| 69 | -cyclopropyl | 9 |
| 70 | -cyclobutyl | 9 |
| 71 | -cyclopentyl | 9 |
| 72 | —CH₂CH₃ | 9 |
| 73 | —CH₂CH₂OH | 9 |
| 74 | —CH(CH₃)CH₂OH (R)-isomer | 9 |
| 75 | —CH(CH₃)CH₂OH | 9 |
| 76 | —CH(CH₃)CH₂OH (S)-isomer | 9 |
| 77 | —CH₂CF₃ | 9 |
| 78 | —CH₂Ph | 9 |

†Ph = phenyl.

In the compounds of formulas X and XI, P is an amino-protecting group. In one embodiment, P is an acid labile amino-protecting group (Pᵃ). In another embodiment, P is selected from benzyl, 4-methoxybenzyl, 2,4-dimethoxybenzyl, diphenylmethyl, triphenylmethyl, methoxycarbonyl, ethoxycarbonyl, tert-butoxycarbonyl, benzyloxycarbonyl, p-methoxybenzyloxycarbonyl, 9-fluorenylmethoxycarbonyl, formyl, acetyl, trimethylsilyl and tert-butyldimethylsilyl. In a particular embodiment, P is tert-butoxycarbonyl.

In the compounds of formula XI, L is a leaving group. In one embodiment, L is chloro, bromo or iodo. In another embodiment, L is methanesulfonyloxy (mesylate) or p-toluenesulfonyloxy (tosylate). In a particular embodiment, L is p-toluenesulfonyloxy.

In one embodiment, Rᶠ is methyl or ethyl. In another embodiment, both Rᶠ groups are joined to form —(CH₂)₂— or —(CH₂)₃—.

Particular compounds of formula X of interest are:
2-[(S)-1-(8-N-Benzyl-N-methylaminooctyl)pyrrolidin-3-yl]-2,2-diphenylacetamide; and
2-{(S)-1-[8-(N-tert-Butoxycarbonyl-N-methylamino)octyl]pyrrolidin-3-yl}-2,2-diphenylacetamide.

Particular compounds of formula XI of interest are:
8-(N-benzyl-N-methylamino)octan-1-ol;
8-(N-tert-butoxycarbonyl-N-methylamino)octan-1-ol; and
toluene-4-sulfonic acid 8-(N-tert-butoxycarbonyl-N-methylamino)octyl ester.

Definitions

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "pharmaceutically-acceptable salt" means a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include ammonium, calcium, copper, ferric, ferrous, lithium, magnesium, manganic, manganous, potassium, sodium, zinc and the like. Particular salts of interest are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, edisylic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, pamoic, pantothenic, phosphoric, succinic, sulfuric, tartaric, p-toluenesulfonic, xinafoic and the like. Particular salts of interest are citric, hydrobromic, hydrochloric, isethionic, maleic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

The term "solvate" means a complex or aggregate formed by one or more molecules of a solute, i.e. a compound of formula I or a pharmaceutically-acceptable salt thereof, and one or more molecules of a solvent. Such solvates are typically crystalline solids having a substantially fixed molar ratio of solute and solvent. This term also includes clathrates, including clathrates with water. Representative solvents include, by way of example, water, methanol, ethanol, isopropanol, acetic acid and the like. When the solvent is water, the solvate formed is a hydrate.

The term "bronchoprotection" or "bronchoprotective" means preventing, ameliorating, suppressing or alleviating the symptoms of a respiratory disease or disorder. For purposes of determining the duration of bronchoprotection, the guinea pig model of acetylcholine-induced bronchoconstriction is used unless otherwise indicated.

The term "therapeutically effective amount" means an amount sufficient to effect treatment when administered to a patient in need of treatment.

The term "treating" or "treatment" as used herein means the treating or treatment of a disease or medical condition (such as COPD or asthma) in a patient, such as a mammal (particularly a human or a companion animal) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, N.Y., 1999, and references cited therein.

The term "amino-protecting group" means a protecting group suitable for preventing undesired reactions at an amino group. Representative amino-protecting groups include, but are not limited to, benzyl, tert-butoxycarbonyl (BOC), trityl (Tr), benzyloxycarbonyl (Cbz), p-methoxybenzyloxycarbonyl (Moz), 9-fluorenylmethoxycarbonyl (Fmoc), formyl, acetyl, trimethylsilyl (TMS), tert-butyldimethylsilyl (TBS), and the like. The term "acid labile amino-protecting group" means an amino-protecting group that is removed by treatment with an acid including, for example, a mineral acid or an organic acid, such as a carboxylic acid or a sulfonic acid. Representative acid labile amino-protecting groups include, but are not limited to, carbamates such as tert-butoxycarbonyl (BOC), p-methoxybenzyloxycarbonyl (Moz) and the like.

The term "carboxy-protecting group" means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluroenylmethyl (Fm), trimethylsilyl (TMS), tert-butyldimethylsilyl (TBS), diphenylmethyl (benzhydryl, DPM) and the like.

The term "optionally substituted" means that the specified group or moiety, such as an alkyl group, phenyl group and the like, is unsubstituted or is substituted with the specified substituents.

General Synthetic Procedures

The substituted pyrrolidine and related compounds of this invention can be prepared from readily available starting materials using the following general methods and procedures. Although a particular embodiment of the present invention may be shown or described in the Schemes below, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. The optimum reaction conditions may vary with the particular reactants or solvent used, but such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, N.Y., 1999, and references cited therein.

The compounds of formula I or salts thereof can be prepared by a process comprising:

(a) reacting a compound of formula III:

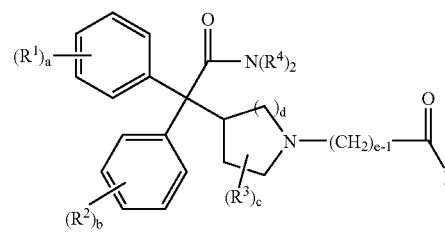

with a compound of formula IV:

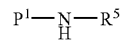

wherein $P^1$ is an amino-protecting group, in the presence of a reducing agent;

(b) reacting a compound of formula V:

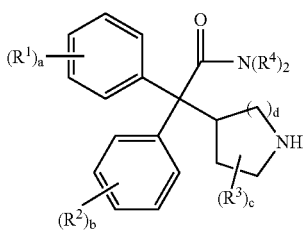

with a compound of formula VI:

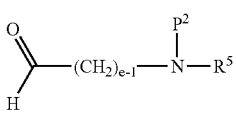

wherein $P^2$ is an amino-protecting group, in the presence of a reducing agent;

(c) reacting a compound of formula VII:

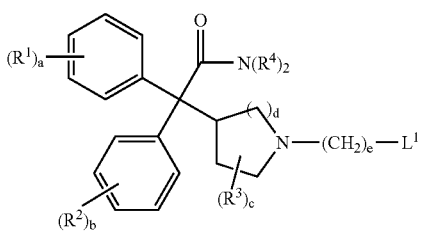

wherein $L^1$ is a leaving group, with a compound of formula IV; or (d) reacting a compound of formula V with a compound of formula VIII:

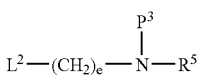

wherein $L^2$ is a leaving group and $P^3$ is an amino-protecting group; and then (e) removing protecting group $P^1$, $P^2$ or $P^3$ to provide a compound of formula I or a salt thereof; wherein $R^{1-5}$ and a-e are as defined herein.

Optionally, a pharmaceutically-acceptable salt of the compound of formula I can be prepared directly in step (e) or, as a separate additional step, from the product of step (e).

In process (a), $P^1$ can be any suitable amino-protecting group, such as benzyl and the like. The reducing agent can be any suitable reducing agent, including metal hydride reducing agents, such as sodium triacetoxyborohydride, sodium cyanoborohydride and the like. Upon completion of the reaction, the amino-protecting group, $P^1$, can be removed using conventional procedures and reagents. For example, a benzyl protecting group can be removed by hydrogenolysis in the presence of a catalyst, such as pallidum.

In process (b), $P^2$ can be any suitable amino-protecting group, such as benzyl, tert-butoxycarbonyl, benzyloxycarbonyl, 9-fluorenylmethoxycarbonyl, tert-butyldimethylsilyl and the like. The reducing agent can be any suitable reducing agent, including metal hydride reducing agents, such as sodium triacetoxyborohydride, sodium cyanoborohydride and the like. Upon completion of the reaction, the amino-protecting group, $P^2$, can be removed using conventional procedures and reagents. For example, a benzyl protecting group can be removed by hydrogenolysis in the presence of a catalyst, such as pallidum; a tert-butoxycarbonyl group can be removed by treatment with acid, such as hydrochloric acid, p-toluenesulfonic acid and the like; a tert-butyldimethylsilyl group can be removed by treatment with a source of fluoride ions, such as triethylamine trihydrofluoride.

In process (c), $L^1$ can be any suitable leaving group including, but not limited to halo, such as chloro, bromo or iodo, or a sulfonic ester group, such as mesylate, tosylate and the like; and $P^1$ is as defined herein.

In process (d), $L^2$ can be any suitable leaving group including, but not limited to, halo, such as chloro, bromo or iodo, or a sulfonic ester group, such as mesylate, tosylate and the like; and $P^3$ can be any suitable amino-protecting group, such as benzyl, tert-butoxycarbonyl, benzyloxycarbonyl, 9-fluorenylmethoxycarbonyl, tert-butyldimethylsilyl and the like. The reducing agent can be any suitable reducing agent, including metal hydride reducing agents, such as sodium triacetoxyborohydride, sodium cyanoborohydride and the like. Upon completion of the reaction, the amino-protecting group, $P^2$, can be removed using conventional procedures and reagents. For example, a benzyl protecting group can be removed by hydrogenolysis in the presence of a catalyst, such as pallidum; a tert-butoxycarbonyl group can be removed by treatment with acid, such as hydrochloric acid, p-toluenesulfonic acid and the like; a tert-butyldimethylsilyl group can be removed by treatment with a source of fluoride ions, such as triethylamine trihydrofluoride.

In particular embodiments of processes (b) and (d), $P^2$ and $P^3$ are a tert-butoxycarbonyl group which is removed by treatment with a pharmaceutically-acceptable acid to generate in situ a pharmaceutically-acceptable salt of the compound of formula I.

By way of further illustration, the preparation of representative compounds of formula I is shown in Scheme A (where the substituents and variables shown in the following Schemes have the definitions provided herein unless otherwise indicated).

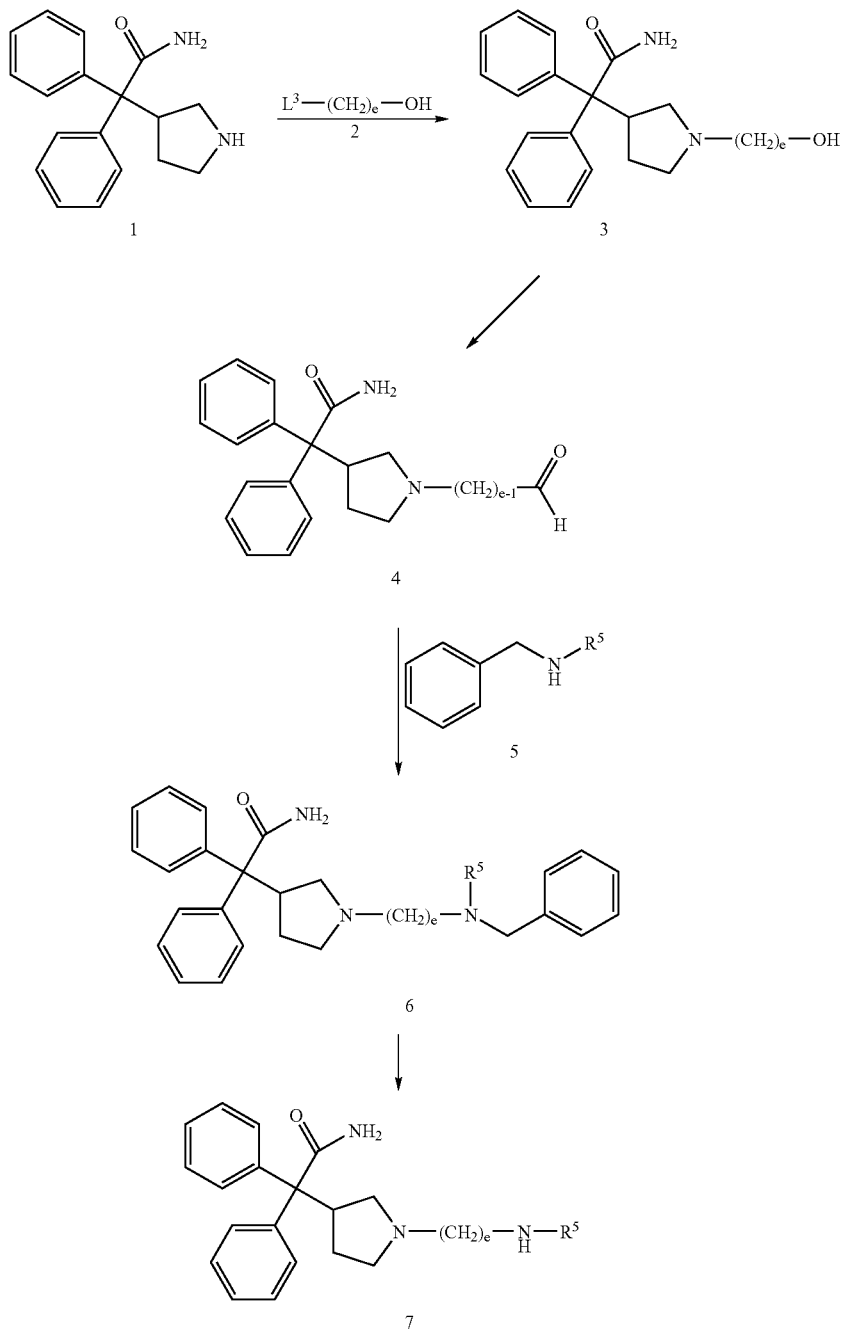

Scheme A

As shown in Scheme A, a compound of formula 1 is first reacted with alcohol 2, where $L^3$ is a suitable leaving group, such as chloro, bromo, iodo, tosyl, mesyl and the like, to provide intermediate 3. Typically, this reaction is conducted by contacting 1 with at least one equivalent, preferably with about 1.0 to about 1.1 equivalents, of alcohol 2 in an inert diluent, such as acetonitrile and the like. This reaction is generally conducted in presence of excess base; preferably, in the presence of about 2 to about 4 equivalent of a base, such as a trialkylamine, preferably triethylamine. Typically, this reaction is conducted at a temperature ranging from about 0° C. to about 80° C., preferably about 40° C. to 50° C., for about 1 to 24 hours, or until the reaction is substantially complete. If desired, the resulting intermediate 3 is readily purified by standard procedures, such as chromatography, recrystallization and the like.

The alcohols of formula 2 used in this reaction are either commercially available or can be prepared from commercially available starting materials and reagents using well-known procedures. Representative alcohols of formula 2 include, by way of example, 8-chloro-1-octanol, 9-chloro-1-nonanol, 8-bromo-1-octanol, 9-bromo-1-nonanol, 8-iodo-1-octanol, 9-iodo-1-nonanol and the like.

The hydroxyl group of intermediate 3 is then oxidized to the corresponding aldehyde to provide intermediate 4. This reaction is typically conducted by contacting 3 with an excess amount of a suitable oxidizing agent. Any oxidizing agent capable of oxidizing a hydroxyl group to an aldehyde may be used in this reaction including chromium (VI) reagents, such as dipyridine chromium (VI) oxide, pyridinium chlorochromate, pyridinium dichromate and the like; and activated dimethyl sulfoxide reagents, such oxalyl chloride/DMSO, sulfur trioxide pyridine complex/DMSO/trialkylamine and the like.

Preferably, this reaction is conducted using an excess of sulfur trioxide pyridine complex and dimethyl sulfoxide in the presence of a trialkylamine, such as triethylamine, diisopropylethylamine and the like. Typically, this reaction is conducted by contacting 3 with about 2.5 to about 3.5 equivalents of sulfur trioxide pyridine complex and an excess, preferably about 10 equivalents, of dimethyl sulfoxide in the presence of an excess, preferably about 5 equivalents, of diisopropylethylamine in an inert diluent, such as dichloromethane. This reaction is generally conducted at a temperature ranging from about −30° C. to about 0° C., preferably at about −10° C. to about −20° C., for about 0.25 to about 2 hours, or until the reaction is substantially complete. Optionally, the resulting aldehyde intermediate 4 is then purified using standard procedures, such as chromatography, recrystallization and the like.

Alternatively, aldehyde intermediate 4 can be prepared by first reacting 1 with a compound of the formula:

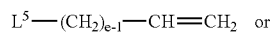
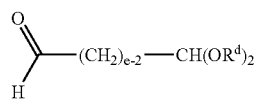

wherein $L^4$ and $L^5$ are suitable leaving groups, such as chloro, bromo, iodo, tosyl, mesyl and the like, e is as defined herein, and each $R^d$ is independently $C_{1-6}$ alkyl or both $R^d$ groups are joined to form $C_{2-6}$ alkylene. Subsequent, hydrolysis of the acetal (i.e., using aqueous acid) or ozonolysis of the olefin (i.e., using $O_3$, followed by decomposition of the ozonide with a reducing agent, such as trimethyl phosphite, dimethyl sulfide and the like) then affords aldehyde 4.

Aldehyde intermediate 4 is then coupled with amine 5 to afford a compound of formula 6. Typically, this reaction is conducted by contacting aldehyde 4 with an excess, such as about 1.0 to about 1.2 equivalents, of 5 in the presence of an excess, preferably about 1.2 to about 1.5 equivalent, of a suitable reducing agent in an inert diluent, such as dichloromethane. Suitable reducing agents include, by way of illustration, sodium triacetoxyborohydride, sodium cyanoborohydride and the like. Preferably, the reducing agent is sodium triacetoxyborohydride. Generally, this reaction is conducted at a temperature ranging from about 0° C. to about 30° C. for about 6 to about 24 hours, or until the reaction is substantially complete. The resulting compound of formula 6 is typically purified using standard procedures, such as chromatography, recrystallization and the like.

Removal of the benzyl group from 6 using conventional reagents and reaction conditions then affords 7. For example, hydrogenolysis of 6 using a catalyst, such as palladium on carbon and/or palladium hydroxide, readily removes the benzyl group to provide 7. Typically, this reaction is conducted by contacting 6 with hydrogen at a pressure ranging from about 40 to about 60 psi in the presence of a catalyst, such as 10% palladium on carbon. This reaction is generally conducted in an inert diluent, such as ethanol or isopropanol, at ambient temperature for about 12 to 120 hours, or until the reaction is substantially complete.

Alternatively, aldehyde intermediate 5 can be reacted with an amine of the formula $R^5$—$NH_2$, where $R^5$ is as defined herein, to afford compound 7 directly. Additionally, if desired, other amino-protecting groups may be used in place of the benzyl group in Scheme A.

The amine compounds suitable for use in the reactions described herein are either commercially available or can be prepared from commercially available starting materials and reagents using well-known procedures. Representative amines suitable for use include, but are not limited to, N-methyl-N-benzylamine, N-ethyl-N-benzylamine, methylamine, ethylamine, n-propylamine, isopropylamine, 2-hydroxyethylamine, DL-2-amino-1-propanol, (R)-(−)-2-amino-1-propanol, (S)-(+)-2-amino-1-propanol, 2,2,2-trifluoroethylamine, benzylamine, cyclopropylamine, cyclobutylamine, cyclopentylamine and the like.

The compounds of formula 1 employed in the reactions described herein are readily prepared by the procedures illustrated in Scheme B.

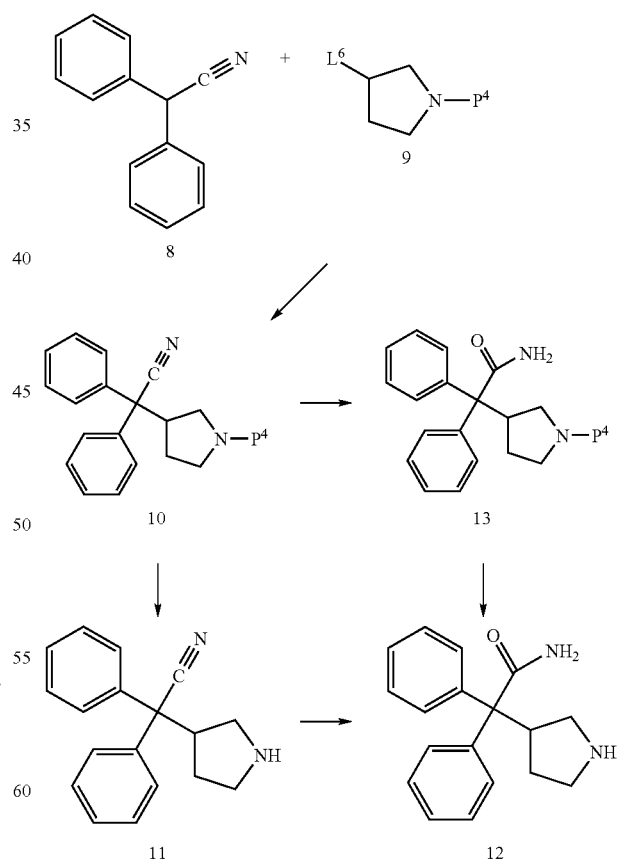

Scheme B

As illustrated in Scheme B, diphenylacetonitrile 8 is reacted with intermediate 9, where $L^6$ is a suitable leaving group, such as chloro, bromo, iodo, tosyl, mesyl and the like, and $P^4$ is an amino-protecting group, such as benzyl, 4-methoxybenzyl, 4-nitrobenzyl, ethoxycarbonyl, phenylcarbonyl and the like, to provide intermediate 10. Typically, this reaction is conducted by first forming the anion of compound 8 by contacting 8 with excess, preferably about 1.4 to about 1.6 equivalents, of a strong base, such as potassium tert-butoxide, in an inert diluent, such as tetrahydrofuran, at a temperature ranging from about −10° C. to about 10° C. for about 0.5 to about 2.0 hours. The resulting anion is then reacted in situ with about 0.95 to about 1.05 equivalents of 9 at a temperature ranging from about 20° C. to about 50° C. for about 10 to about 48 hours, or until the reaction is substantially complete. Compounds of formula 9, where $L^6$ is a sulfonate ester leaving group, are readily prepared from the corresponding alcohol using conventional procedures and reagents. For example, (S)-1-benzyl-3-pyrrolidinol is readily converted to (S)-1-benzyl-3-(p-toluenesulfonyloxy) pyrrolidine by treatment with about 1.1 equivalents of p-toluenesulfonyl chloride and about 1.2 equivalents of 1,4-diazabicyclo[2.2.2]octane (DABCO). Other compounds of formula 9 can be prepared by similar procedures using commercially available starting materials and reagents.

Compound 10 is then deprotected using conventional procedures and reagents to afford compound 11. For example, if $P^4$ in compound 10 is a benzyl protecting group, the benzyl group is readily removed by transfer hydrogenolysis using a hydrogen source, such as ammonium formate, and a catalyst, such as palladium on carbon. Preferably, this reaction is conducted using the hydrochloride or hydrobromide salt of compound 10 or in the presence of an acid, such as hydrochloric acid, hydrobromic acid, formic acid, sulfuric acid, phosphoric acid, p-toluenesulfonic acid, acetic acid, oxalic acid and the like. This hydrogenolysis reaction can also be conducted using hydrogen and a catalyst in the presence of an acid. See, for example, U.S. Pat. No. 6,005,119, issued Dec. 21, 1999 to N. Mori et al.

The nitrile group of compound 11 is then hydrolyzed to the corresponding amide (i.e., —C(O)NH$_2$) to provide a compound of formula 10. This reaction is typically conducted by contacting 11 with aqueous sulfuric acid, preferably 80% sulfuric acid, at a temperature ranging from about 70° C. to about 100° C., preferably about 90° C., for about 12 to about 36 hours, or until the reaction is substantially complete. As shown in Scheme B, hydrolysis of the nitrile group to the amide can also be performed before removal of the protecting group to afford 13, which can then be deprotected to provide compound 12.

If desired, the nitrile group of compound 10 or 11 can be hydrolyzed to the corresponding carboxylic acid (i.e., —COOH) using, for example, aqueous sodium hydroxide containing about 6 to about 12% hydrogen peroxide. The resulting carboxylic acid can then be coupled to various amines (i.e., $R^eCR^eNH$, where $R^e$ is as defined herein) to form substituted amides using well-known procedures and reagents.

Compounds of this invention can also be prepared by the procedure illustrated in Scheme C.

Scheme C

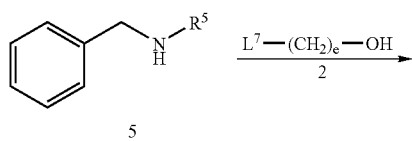

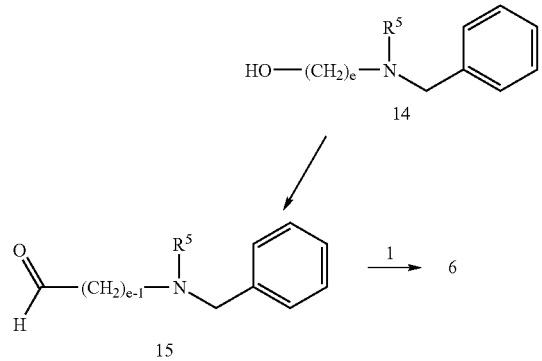

As shown in Scheme C, alcohol 2, where $L^7$ is a suitable leaving group, such as chloro, bromo, iodo, tosyl, mesyl and the like, can be reacted with benzylamine 5 to provide intermediate 14. Typically, this reaction is conducted by contacting alcohol 2 with at least one equivalent, preferably with about 1.0 to about 1.1 equivalents, of benzylamine 5 in an inert diluent, such as acetonitrile and the like. This reaction is generally conducted in presence of excess base; preferably, in the presence of about 2 to about 4 equivalent of a base, such as a trialkylamine, preferably triethylamine. Typically, this reaction is conducted at a temperature ranging from about 0° C. to about 80° C., preferably about 40° C. to 60° C., for about 1 to 24 hours, or until the reaction is substantially complete. If desired, the resulting intermediate 14 is readily purified by standard procedures, such as chromatography, recrystallization and the like.

The hydroxyl group of intermediate 14 is then oxidized to the corresponding aldehyde to provide intermediate 15. This reaction is typically conducted by contacting 14 with an excess amount of a suitable oxidizing agent. Any oxidizing agent capable of oxidizing a hydroxyl group to an aldehyde may be used in this reaction including chromium (VI) reagents, such as dipyridine chromium (VI) oxide, pyridinium chlorochromate, pyridinium dichromate and the like; and activated dimethyl sulfoxide reagents, such oxalyl chloride/DMSO, sulfur trioxide pyridine complex/DMSO/trialkylamine and the like.

Preferably, this reaction is conducted using an excess of sulfur trioxide pyridine complex and dimethyl sulfoxide in the presence of a trialkylamine, such as triethylamine, diisopropylethylamine and the like. Typically, this reaction is conducted by contacting 14 with about 2.5 to about 3.5 equivalents of sulfur trioxide pyridine complex and an excess, preferably about 10 equivalents, of dimethyl sulfoxide in the presence of an excess, preferably about 5 equivalents, of diisopropylethylamine in an inert diluent, such as dichloromethane. This reaction is generally conducted at a temperature ranging from about −30° C. to about 0° C., preferably at about −10° C. to about −20° C., for about 0.25 to about 6 hours, or until the reaction is substantially complete. Optionally, the resulting aldehyde intermediate 15 is then purified using standard procedures, such as chromatography, recrystallization and the like.

Aldehyde intermediate 15 is then coupled with 1 to afford a compound of formula 6. Typically, this reaction is conducted by contacting aldehyde 15 with at least about one equivalent of 1 in the presence of an excess, preferably about 1.2 to about 1.5 equivalent, of a suitable reducing agent in an inert diluent, such as dichloromethane. Suitable reducing agents include, by way of illustration, sodium triacetoxyborohydride, sodium cyanoborohydride and the like. Preferably, the reducing agent is sodium triacetoxyborohydride. Generally, this reaction is conducted at a temperature ranging from about 0° C. to about 30° C. for about 2 to about 24 hours, or until the reaction is substantially complete. The resulting compound of formula 6 is typically purified using standard procedures, such as chromatography, recrystallization and the like. The benzyl group can then be removed from 6 to afford 7 as discussed above.

Additionally, it will also be appreciated by those skilled in the art that the synthetic steps illustrated in Schemes A, B and C can be conducted in a different order from that shown, or by using different reagents from those described, to produce the compounds of formula 7. For example, instead of oxidizing the hydroxyl group of intermediate 3 or 14 to an aldehyde, these hydroxyl groups can be converted into a leaving group, such as a chloro, bromo, iodo, mesylate or tosylate, using conventional reagents and reaction procedures. The resulting leaving group is then readily displaced with amine 5 or intermediate 1 to afford compound 6.

By way of further example, representative compounds of formula I can be prepared as illustrated in Scheme D:

The hydroxyl group of compound 16 is then converted into a leaving group, such as a chloro, bromo, iodo, mesylate or tosylate, using conventional reagents and reaction procedures to provide a compound of formula 17. For example, the hydroxyl group is converted to a tosylate leaving group by reaction with tosyl chloride (p-toluenesulfonyl chloride) in the presence of a suitable base including tertiary amines, such as 1,4-diazabicyclo[2.2.2]octane. This reaction is typically conducted in an inert diluent, such as methyl tert-butyl ether, at a temperature ranging from about 0° C. to about 30° C. for 0.5 to 6 hours, or until the reaction is substantially complete.

The leaving group of compound 17 is then displaced with a compound of formula 1 to provide a compound of formula 18. This reaction is typically conducted by contacting 17 with about 0.95 to about 1.1 molar equivalents of 1 in the presence of a tertiary amine, such as diisopropylethylamine. The reaction is generally conducted in an inert diluent, such as acetonitrile, at a temperature ranging from about 25° C. to about 100° C. for about 2 to about 12 hours, or until the reaction is substantially complete.

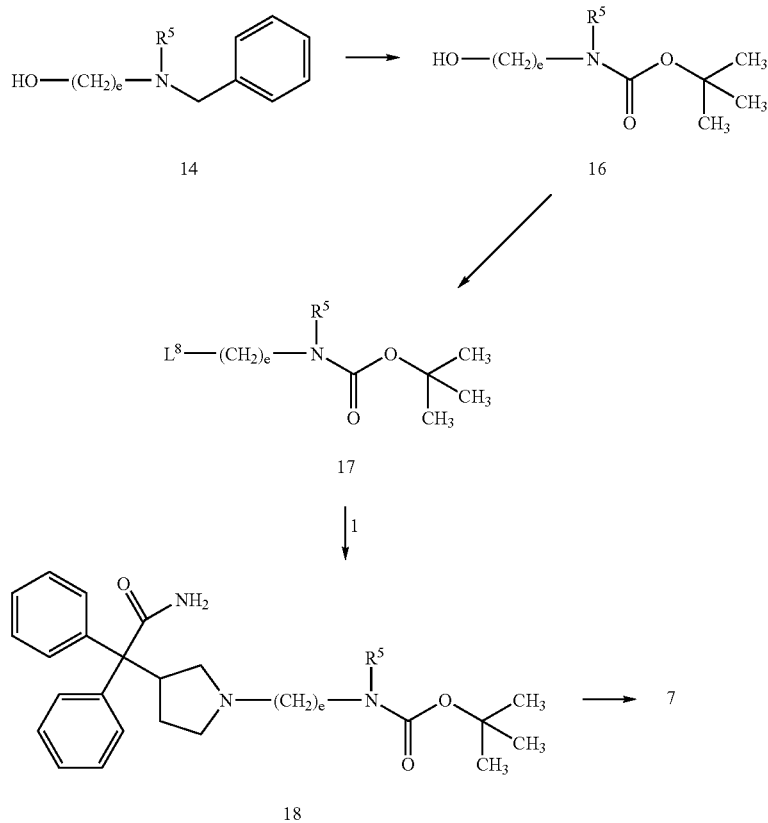

As shown in Scheme D, the benzyl amino-protecting group of compound 14 can be removed and replaced with a tert-butoxycarbonyl amino-protecting group using conventional procedures and reagents (i.e., hydrogenolysis to remove the benzyl group and di-tert-butyl dicarbonate to form the tert-butoxycarbonyl group) to provide compound 16.

The tert-butoxycarbonyl amino-protecting group of compound 18 is then removed using conventional reagents and reaction conditions to afford a compound of formula 7 or a salt thereof. For example, the tert-butoxycarbonyl amino-protecting group can be readily removed by treatment with an acid, such as hydrochloric acid, trifluoroacetic acid, p-toluenesulfonic acid and the like.

In one embodiment, the compound of formula 18 is contacted with a pharmaceutically-acceptable acid to generate a pharmaceutically-acceptable salt of compound 7 directly without isolation of the free-base. For example, 18 can be contacted with naphthalene-1,5-disulfonic acid to form the naphthalene-1,5-disulfonic acid salt of compound 7. This reaction is typically conducted by contacting 18 with about 1 to about 3 equivalents, such as 2 equivalents, of naphthalene-1,5-disulfonic acid in an inert diluent, such as isopropanol. In one embodiment, isopropanol containing about 2 to about 10% by volume water is employed as the diluent to provide a crystalline naphthalene-1,5-disulfonic acid salt.

Further details regarding specific reaction conditions and other procedures for preparing representative compounds of this invention or intermediates thereto are described in the Examples set forth below.

Pharmaceutical Compositions

The substituted pyrrolidine and related compounds of this invention are typically administered to a patient in the form of a pharmaceutical composition. Such pharmaceutical compositions may be administered to the patient by any acceptable route of administration including, but not limited to, oral, inhaled, nasal, topical (including transdermal) and parenteral modes of administration.

It will be understood that any form of the compounds of this invention, (i.e., free base, pharmaceutically-acceptable salt, or solvate) that is suitable for the particular mode of administration can be used in the pharmaceutical compositions discussed herein.

Accordingly, in one of its compositions aspects, this invention is directed to a pharmaceutical composition comprising a pharmaceutically-acceptable carrier or excipient and a therapeutically effective amount of a compound of formula I or II, or a pharmaceutically acceptable salt thereof. Optionally, such pharmaceutical compositions may contain other therapeutic and/or formulating agents if desired.

The pharmaceutical compositions of this invention typically contain a therapeutically effective amount of a compound of the present invention or a pharmaceutically-acceptable salt thereof. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington: The Science and Practice of pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by throughly and intimately mixing or blending a compound of the invention with a pharmaceutically-acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are provided commercially, for example by PARI GmbH (Starnberg, German). Other nebulizer devices are disclosed, for example, in U.S. Pat. No. 6,123,068 and WO 97/12687.

A representative pharmaceutical composition for use in a nebulizer inhaler comprises an isotonic aqueous saline solution comprising from about 0.05 μg/mL to about 10 mg/mL of a compound of formula I or a pharmaceutically-acceptable salt or solvate or stereoisomer thereof. In one embodiment, the pH of this composition is in the range of from about 4 to about 6. In a particular embodiment, this composition is optionally buffered using citrate buffer to a pH of about 5.

In another specific embodiment of this invention, the pharmaceutical composition comprising the active agent is administered by inhalation using a dry powder inhaler. Such dry powder inhalers typically administer the active agent as a free-flowing powder that is dispersed in a patient's airstream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 µm and about 100 µm and micronized particles of a compound of formula I, or a pharmaceutically-acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically-acceptable salt thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3,-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a compound of formula I, or a pharmaceutically-acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of an metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetra acetic acid (EDDA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When intended for oral administration, the pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipients. For example, a compound of this invention can be admixed with permeation enhancers, such as propylene glycol, polyethylene glycolm monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of formula I, or pharmaceutically-acceptable salt or solvate or stereoisomer thereof. For example, the pharmaceutical compositions of this invention may further comprise one or more therapeutic agents selected from $\beta_2$ adrenergic receptor agonists, anti-inflammatory agents (e.g. corticosteroids and non-steroidal anti-inflammatory agents (NSAIDs), other muscarinic receptor antagonists (i.e., anticholinergic agents), antiinfective agents (e.g. antibiotics or antivirals) and antihistamines. The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically-acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino)hexyl]oxy}butyl)benzenesulfonamide and 3-(-3-{[7-({(2R)-2-hydroxy-2-[4-hydroxy-3-(hydroxymethyl)phenyl]ethyl}amino)heptyl]oxy}-propyl)benzenesulfonamide and related compounds disclosed in WO 02/066422, published on Aug. 29, 2002; 3-[3-(4-{[6-([{(2R)-2-hydroxy-2-[4-hydroxy-3-(hydroxymethyl)phenyl]ethyl}amino)hexyl]oxy}butyl)phenyl]imidazolidine-2,4-dione and related compounds disclosed in WO 02/070490, published Sep. 12, 2002; 3-(4-{[6-({(2R)-2-[3-(formylamino)-4-hydroxyphenyl]-2-hydroxyethyl}amino)hexyl]oxy}butyl)benzenesulfonamide, 3-(4-{[6-({(2S)-2-[3-(formylamino)-4-hydroxyphenyl]-2-hydroxyethyl}amino)hexyl]oxy}butyl)benzenesulfonamide, 3-(4-{[6-({(2R/S)-2-[3-(formylamino)-4-hydroxyphenyl]-2-hydroxyethyl}amino)hexyl]oxy}butyl)benzenesulfonamide, N-(tert-butyl)-3-(4-{[6-({(2R)-2-[3-(formylamino)-4-hydroxyphenyl]-2-hydroxyethyl}amino)hexyl]-oxy}butyl)benzenesulfonamide, N-(tert-butyl)-3-(4-{[6-({(2S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl)benzenesulfonamide and related compounds disclosed in WO 02/076933, published on Oct. 3, 2002; 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439, published on Mar. 27, 2003; N-{2-[4-((R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 B1, issued on Jun. 10, 2003; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 B2, issued on Nov. 25, 2003; and pharmaceutically-acceptable salts thereof. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 μg to about 500 μg per dose.

Representative corticosteroids that can be used in combination with the compounds of this invention include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. When employed, the corticosteroid will be present in the pharmaceutical composition in a therapeutically effective amount. Typically, the steroidal anti-inflammatory agent will be present in an amount sufficient to provide from about 0.05 μg to about 500 μg per dose.

Other suitable combinations include, for example, other anti-inflammatory agents, e.g., NSAIDs (such as sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically-acceptable salt thereof; or, for those compounds listed as a salt, alternate pharmaceutically-acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically-acceptable salt thereof; or, for those compounds listed as a salt, alternate pharmaceutically-acceptable salt thereof.

Suitable doses for the other therapeutic agents administered in combination with a compound of the invention are in the range of about 0.05 μg/day to about 100 mg/day.

The following formulations illustrate representative pharmaceutical compositions of the present invention:

FORMULATION EXAMPLE A

Hard gelatin capsules for oral administration are prepared as follows:

| Ingredients | Amount |
| --- | --- |
| Compound of the invention | 250 mg |
| Lactose (spray-dried) | 200 mg |
| Magnesium stearate | 10 mg |

Representative Procedure: The ingredients are throughly blended and then loaded into a hard gelatine capsule (460 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are throughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 100 mg |
| Polyoxyethylene sorbitan monooleate | 50 mg |
| Starch powder | 250 mg |

Representative Procedure: The ingredients are throughly blended and then loaded into a gelatin capsule (300 mg of composition per capsule).

FORMULATION EXAMPLE D

Tablets for oral administration are prepared as follows:

| Ingredients | Amount |
| --- | --- |
| Compound of the invention | 10 mg |
| Starch | 45 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The compound of the invention, starch and cellulose are passed through a No. 45 mesh U.S. sieve and mixed throughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 250 mg |
| Microcrystalline cellulose | 400 mg |
| Silicon dioxide fumed | 10 mg |
| Stearic acid | 5 mg |

Representative Procedure: The ingredients are throughly blended and then compressed to form tablets (665 mg of composition per tablet).

FORMULATION EXAMPLE F

Single-scored tablets for oral administration are prepared as follows:

| Ingredients | Amount |
| --- | --- |
| Compound of the invention | 400 mg |
| Cornstarch | 50 mg |
| Croscarmellose sodium | 25 mg |
| Lactose | 120 mg |
| Magnesium stearate | 5 mg |

Representative Procedure: The ingredients are throughly blended and compressed to form a single-scored tablet (600 mg of compositions per tablet).

FORMULATION EXAMPLE G

A suspension for oral administration is prepared as follows:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

FORMULATION EXAMPLE H

A dry powder for administration by inhalation is prepared as follows:

| Ingredients | Amount |
| --- | --- |
| Compound of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

FORMULATION EXAMPLE I

A dry powder formulation for use in a dry powder inhalation device is prepared as follows:

Representative Procedure: A pharmaceutical composition is prepared having a bulk formulation ratio of micronized compound of the invention to lactose of 1:200. The composition is packed into a dry powder inhalation device capable of delivering between about 10 and about 100 µg of the compound of the invention per dose.

FORMULATION EXAMPLE J

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of the compound of the invention as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

FORMULATION EXAMPLE K

A pharmaceutical composition for use in a metered dose inhaler is prepared as follows:

Representative Procedure: A suspension containing 5% compound of the invention, 0.5% lecithin, and 0.5% trehalose is prepared by dispersing 5 g of active ingredient as micronized particles with mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

FORMULATION EXAMPLE L

A pharmaceutical composition for use in a nebulizer inhaler is prepared as follows:

Representative Procedure: An aqueous aerosol formulation for use in a nebulizer is prepared by dissolving 0.1 mg of the compound of the invention in 1 mL of a 0.9% sodium chloride solution acidified with citric acid. The mixture is stirred and sonicated until the active ingredient is dissolved. The pH of the solution is adjusted to a value of about 5 by the slow addition of NaOH.

FORMULATION EXAMPLE M

An injectable formulation is prepared as follows:

| Ingredients | Amount |
|---|---|
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The substituted pyrrolidine and related compounds of this invention are useful as muscarinic receptor antagonists and therefore, such compounds are useful for treating medical conditions mediated by muscarinic receptors, i.e., medical conditions which are ameliorated by treatment with a muscarinic receptor antagonist. Such medical conditions include, by way of example, respiratory tract disorders, such as chronic obstructive pulmonary disease, asthma, pulmonary fibrosis, allergic rhinitis, rhinorrhea; genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; cardiac arrhythmias, such as sinus bradycardia; Parkinson's disease; cognitive disorders, such as Alzheimer's disease; dismenorrhea; and the like.

In one embodiment, the compounds of this invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome.

When used to treat smooth muscle disorders or other conditions mediated by muscarinic receptors, the compounds of this invention will typically be administered orally, rectally, parenterally or by inhalation in a single daily dose or in multiple doses per day. The amount of active agent administered per dose or the total amount administered per day will typically be determined by the patient's physician and will depend on such factors as the nature and severity of the patients condition, the condition being treated, the age and general health of the patient, the tolerance of the patient to the active agent, the route of administration and the like.

Typically, suitable doses for treating smooth muscle disorders or other disorders mediated by muscarinic receptors will range from about 0.14 μg/kg/day to about 7 mg/kg/day of active agent; including from about 0.15 μg/kg/day to about 5 mg/kg/day. For an average 70 kg human, this would amount to about 10 μg per day to about 500 mg per day of active agent.

In a specific embodiment, the compounds of this invention are useful for treating respiratory disorders, such as COPD or asthma, in mammals including humans. When used to treat respiratory disorders, the compounds of this invention will typically be administered by inhalation in multiple doses per day, in a single daily dose or a single weekly dose. Generally, the dose for treating a respiratory disorder will range from about 10 μg/day to about 200 μg/day.

When used to treat a respiratory disorder, the compounds of this invention are optionally administered in combination with other therapeutic agents such as a $\beta_2$-adrenoreceptor agonist; a corticosteroid, a non-steroidal anti-inflammatory agent, or combinations thereof.

In another embodiment, the compounds of this invention are used to treat overactive bladder. When used to treat overactive bladder, the compounds of this invention will typically be administered orally in a single daily dose or in multiple doses per day; preferably in a single daily dose. Preferably, the dose for treating overactive bladder will range from about 1.0 mg/day to about 500 mg/day.

In yet another embodiment, the compounds of this invention are used to treat irritable bowel syndrome. When used to treat irritable bowel syndrome, the compounds of this invention will typically be administered orally or rectally in a single daily dose or in multiple doses per day. Preferably, the dose for treating irritable bowel syndrome will range from about 1.0 mg/day to about 500 mg/day.

Since compounds of this invention are muscarinic receptor antagonists, such compounds are also useful as research tools for investigating or studying biological systems or samples having muscarinic receptors. Such biological systems or samples may comprise $M_1$, $M_2$, $M_3$, $M_4$ and/or $M_5$ muscarinic receptors. Any suitable biological system or sample having muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a muscarinic receptor is contacted with a muscarinic receptor-antagonizing amount of a compound of this invention. The effects of antagonizing the muscarinic receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio) triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.). A compound of this invention will antagonize or decrease the activation of muscarinic receptors in any of the functional assays listed above, or assays of a similar nature. A muscarinic receptor -antagonizing amount of a compound of this invention will typically range from about 0.1 nanomolar to about 100 nanomolar.

Additionally, the compounds of this invention can be used as research tools for discovering new compounds that have muscarinic receptor antagonist activity. In this embodiment, muscarinic receptor binding data (for example, as determined by in vitro radioligand displacement assays) for a test compound or a group of test compounds is compared to the muscarinic receptor binding data for a compound of this invention to identify those test compounds that have about equal or superior muscarinic receptor binding, if any. This aspect of the invention includes, as separate embodiments, both the generation of comparison data (using the appropriate assays) and the analysis of the test data to identify test compounds of interest.

Among other properties, compounds of this invention have been found to be potent inhibitors of $M_3$ muscarinic receptor activity. Accordingly, in specific embodiments, this invention is directed to compounds of formula I having an inhibition dissociation constant for the $M_3$ receptor subtype of less than or equal to 100 nM; or less than or equal to 50 nM; or less than or equal to 10 nM (as determined by in vitro radioligand displacement assays).

Additionally, compounds of this invention have also been found to possess a surprising and unexpected duration of bronchoprotection when administered by inhalation. Accordingly, in another specific embodiment, this invention is directed to compounds of formula I having a duration of bronchoprotection greater than about 24 hours, including about 24 hours to about 72 hours, when administered by inhalation. The term "duration of bronchoprotection" means the length of time that a compound provides a bronchoprotective effect in the guinea pig model of acetylcholine-induced bronchoconstriction.

Moreover, compounds of this invention have been found to possess surprising and unexpected lung selectivity when administered by inhalation. Accordingly, in another specific embodiment, this invention is directed to compounds of formula I having an apparent lung-selectivity index greater than 10 at either 1.5 hours or 24 hours post-dosing by inhalation. The term "apparent lung-selectivity index" means either (a) the ratio of the anti-sialagogue $ID_{50}$ (dose required to inhibit pilocaripine-induced salivation by 50%) to the bronchoprotective $ID_{50}$ (dose required to inhibit acetylcholine-induced bronchoconstriction by 50%); or (b) the ratio of the anti-depressor $ID_{50}$ (dose required to inhibit methacholine-induced decrease in mean arterial pressure by 50%) to the bronchoprotective $ID_{50}$ (dose required to inhibit acetylcholine-induced bronchoconstriction by 50%).

These properties, as well as the utility of the compounds of this invention, can be demonstrated using various in vitro and in vivo assays well-known to those skilled in the art. For example, representative assays are described in further detail in the following Examples.

EXAMPLES

The following synthetic and biological examples are offered to illustrate this invention and are not to be construed in any way as limiting the scope of this invention. In the examples below, the following abbreviations have the following meanings unless otherwise indicated. Abbreviations not defined below have their generally accepted meaning.

AC=adenylyl cyclase
ACN=acetonitrile
BSA=bovine serum albumin
BOC=tert-butoxycarbonyl
cAMP=cyclic adenosine monophosphate
CHO=Chinese hamster ovary
cpm=counts per minute
DCM=dichloromethane
DIPEA=diisopropylethylamine
DME=ethylene glycol dimethyl ether
DMF=N,N-dimethylformrnamide
DMSO=dimethyl sulfoxide
dPBS=Dulbecco's phosphate buffered saline, without $CaCl_2$ and MgCl
EDC=1-(3-dimethylaminopropyl)-3-ethylcarbodiimide hydrochloride
EDDA=ethylenediaminetetraacetic acid
EtOAc=ethyl acetate
FBS=fetal bovine serum
GDP=guanosine 5'-diphosphate
HEPES=4-(2-hydroxyethyl)-1-piperazine-ethanesulfonic acid
$hM_1$=human muscarinic receptor subtype 1
$hM_2$=human muscarinic receptor subtype 2
$hM_3$=human muscarinic receptor subtype 3
$hM_4$=human muscarinic receptor subtype 4
$hM_5$=human muscarinic receptor subtype 5
HOAT 1-hydroxy-7-azabenzotriazole
HPLC=high performance liquid chromatography
$K_i$=inhibition dissociation constant
MS=mass spectrometry
MTBE=methyl tert-butyl ether
[$^3$H]NMS=l-[N-methyl-$^3$H]scopolamine methyl chloride
OIS=oxotremorine-induced salivation
PMB=p-methoxybenzyl
PyBOP=benzotriazol-1-yloxytripyrrolidino-phosphonium hexafluorophosphate
THF=tetrahydrofuran
TLC=thin layer chromatography
TFA=trifluoroacetic acid All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification.

Example A

Preparation of 2,2-Diphenyl-2-(S)-pyrrolidin-3-ylacetaniide

Step A—Preparation of
(S)-1-Benzyl-3-(p-toluenesulfonyloxy)pyrrolidine

To a stirred solution of (S)-1-benzyl-3-pyrrolidinol (44.3 g, 0.25 mol) and 1,4-diazabicyclo[2.2.2]octane (33.7 g, 0.3 mol) in 250 mL of tert-butyl methyl ether under an atmosphere of nitrogen at 0° C., was added p-toluenesulfonyl chloride (52.4 g, 0.275 mol) portion-wise over 20 min. The reaction mixture was stirred at 0° C. for 1 h. The ice bath was removed and the mixture was stirred at ambient temperature overnight (20±5 h). Ethyl acetate (100 mL) was added, followed by saturated aqueous sodium bicarbonate solution (250 mL). The resulting mixture was stirred at ambient temperature for 1 h. The layers were separated and the organic layer was washed with saturated aqueous sodium bicarbonate solution (250 mL); saturated aqueous ammonium chloride solution (250 mL); saturated aqueous sodium chloride solution (250 mL); and then dried over sodium sulfate (80 g). The sodium sulfate was filtered off and washed with ethyl acetate (20 mL) and the solvent was removed in vacuo to give 78.2 g of the title intermediate as an off-white solid (94% yield; 95% purity by HPLC).

Step B—Preparation of (S)-1-Benzyl-3-(1-cyano-1,
1-diphenylmethyl)-pyrrolidine

To a stirred solution of diphenylacetonitrile (12.18 g, 61.8 mmol) in anhydrous THF (120 mL) at 0° C., potassium tert-butoxide (10.60 g, 94.6 mmol) was added over 5 min. The reaction mixture was stirred at 0° C. for 1 h. To the reaction mixture at 0° C. was added (S)-1-benzyl-3-(p-toluenesulfonyloxy)-pyrrolidine (20.48 g, 61.3 mmol) in one portion. The cold bath was removed and the reaction mixture was stirred for 5 to 10 min at which time the reaction mixture had become a brown homogeneous solution. The reaction mixture was then heated at 40° C. overnight (20±5 h). The reaction mixture (bright yellow suspension) was allowed to cool to room temperature before adding water (150 mL). Most of the THF was then removed in vacuo and isopropyl acetate (200 mL) was added. The layers were separated and the organic layer was washed with saturated aqueous ammonium chloride solution (150 mL); saturated aqueous sodium chloride solution (150 mL); and then dried over sodium sulfate (50 g). The sodium sulfate was filtered off and washed with isopropyl acetate (20 mL) and the solvent was removed in vacuo to give 23.88 g of the title intermediate as a light brown oil (>99% yield, 75% purity by HPLC, contaminated mainly with excess diphenylacetonitrile).

Step C—Preparation of
(S)-3-(1-Cyano-1,1-diphenylmethyl)pyrrolidine (S)-1-Benzyl-3-(1-cyano-1,1-diphenylmethyl)pyrrolidine was dissolved in isopropyl acetate (ca. 1 g/10 mL) and the solution was mixed with an equal volume of 1N aqueous hydrochloric acid. The resulting layers were separated and the aqueous layer was extracted with an equal volume of isopropyl acetate. The organic layers were combined, dried over sodium sulfate and filtered. The solvent was removed in vacuo to afford (S)-1-benzyl-3-(1-cyano-1,1-diphenylmethyl)pyrrolidine hydrochloride as a light yellow foamy solid. (Note: This hydrochloride salt can also be prepared during the work-up of Step B).

To a stirred solution of (S)-1-benzyl-3-(1-cyano-1,1-diphenylmethyl)pyrrolidine hydrochloride (8.55 g, 21.98 mmol) in methanol (44 mL) was added palladium on carbon (1.71 g) and ammonium formate (6.93 g, 109.9 mmol). The reaction mixture was heated to 50° C. with stirring for 3 h. The reaction was cooled to ambient temperature and water (20 mL) was added. The resulting mixture was filtered through a pad of Celite, washing with methanol (20 mL). The filtrate was collected and most of the methanol was removed in vacuo. The residue was mixed with isopropyl acetate (100 mL) and 10% aqueous sodium carbonate (50 mL). The resulting layers were separated and the aqueous layer was extracted with isopropyl acetate (50 mL). The organic layers were combined and dried over sodium sulfate (20 g). The sodium sulfate was filtered off and washed with isopropyl acetate (20 mL). The solvent was removed in vacuo to afford 5.75 g of the title intermediate as a light yellow oil (99.7% yield, 71% purity by HPLC).

Step D—Preparation of
2,2-Diphenyl-2-(S)-pyrrolidin-3-ylacetamide

A 200 mL flask with a magnetic stir bar and a nitrogen inlet was charged with (S)-3-(1-cyano-1,1-diphenylmethyl)pyrrolidine (2.51 g) and 80% $H_2SO_4$ (19.2 mL; pre-prepared with 16 mL of 96% $H_2SO_4$ and 3.2 mL of $H_2O$). The reaction mixture was then heated at 90° C. for 24 h or until starting material was consumed as indicated by HPLC. The reaction mixture was allowed to cool to room temperature and then poured onto ice (ca. 50 mL by volume). A 50% aqueous sodium hydroxide solution was added slowly to the mixture with stirring over an ice bath until the pH was about 12. Dichloromethane (200 mL) was added and mixed with the aqueous solution at which time sodium sulfate precipitated out and was filtered off. The filtrate was collected and the layers were separated. The aqueous layer was extracted with dichloromethane (100 mL) and the organic layers were combined and dried with over sodium sulfate (5 g). The sodium sulfate was filtered off and washed with dichloromethane (10 mL). The solvent was removed in vacuo to give the crude product as a light yellow foamy solid (ca. 2.2 g, 86% purity by HPLC).

The crude product was dissolved in ethanol (18 mL) with stirring. To this solution was added a warm solution of L-tartaric acid (1.8 g) in ethanol (14 mL) and the resulting mixture was stirred overnight (15±5 h). The resulting precipitate was isolated by filtration to give an off-white solid (ca. 3.2 g, >95% purity by HPLC). Methanol (15 mL) was added to this solid and the resulting slurry was stirred at 70° C. overnight (15 h). The slurry was allowed to cool to ambient temperature and a white solid (~2.6 g, >99% purity by HPLC) was obtained after filtration. To this solid was added ethyl acetate (30 mL) and 1 N aqueous sodium hydroxide (25 mL). This mixture was mixed until two distinct layers formed and then the layers were separated and the aqueous layer was extracted with ethyl acetate (20 mL). The organic layers were combined and dried over sodium sulfate (10 g). The sodium sulfate was removed by filtration and the solvent was evaporated in vacuo to afford 1.55 g of the title intermediate as an off-white foamy solid (58% yield; >99% purity by HPLC).

Example 1

Synthesis of 2-[(S)-1-(8-Methylaminooctyl)pyrrolidin-3-yl]-2,2-diphenylacetamide Step A—Preparation of
8-(N-Benzyl-N-methylamino)octan-1-ol 8-Bromo-1-octanol (25 g, 119.6 mmol) in acetonitrile (50 mL) was added to a stirred solution of N-benzyl-N-methylamine (43.49 g, 358.9 mmol) and potassium carbonate (49.52 g, 358.9 mmol) in acetonitrile (250 mL) at 35° C. The reaction mixture was then stirred at 35° C. for 7 h and then cooled to ambient temperature. The potassium carbonate was filtered and the filtrate was concentrated under reduced pressure. The crude residue was dissolved in MTBE (400 mL) and the organic phase was washed with water, brine and dried over magnesium sulfate. N-methyl-2-pyrrolidone was added and the mixture was concentrated under reduced pressure to remove excess N-benzyl-N-methylamine. MTBE (400 mL) was added and the organic phase was washed with water, brine, and dried over magnesium sulfate, filtered and concentrated under reduced pressure to afford the title intermediate as an oil (~100% conversion).

Analytical Data: MS m/z 250.3 ($MH^+$).

Step B—Preparation of
8-(N-Benzyl-N-methylamino)octanal

Dimethylsulfoxide (22.71 mL, 320 mmol) and then diisopropylethylamine (55.74 mL, 320 mmol) were added to a stirred solution of the intermediate from Step A (20 g, 80 mmol) in dichloromethane (200 mL) at −10° C. The reaction mixture was stirred at −10° C. for 30 min, then sulfur trioxide pyridine complex (38 g, 240 mmol) was added portionwise. The reaction mixture was stirred for an additional 1 h at −10° C. and then water (200 mL) was added. The organic layer was separated and washed with water (200 mL), brine (30 mL), dried over magnesium sulfate and then concentrated under reduced pressure. Toluene (100 mL) was added and removed under reduced pressure to afford the title intermediate as oil (~100% conversion).

Step C—Preparation of 2-[(S)-1-(8-N-Benzyl-N-methylaminooctyl)pyrrolidin-3-yl]-2,2-diphenylacetamide A solution of the intermediate from Step B (5.95 g, 24 mmol) and 2,2-diphenyl-2-(S)-pyrrolidin-3-ylacetamide (7.4 g, 26.4 mmol) in dichloromethane (250 mL) was cooled at 0° C. and stirred for 10 min. Sodium triacetoxyborohydride (8.4 g, 36 mmol) was added portionwise at 0° C. and the reaction mixture was stirred at room temperature for 4 h. Dichloromethane was added and the organic phase was washed with sodium bicarbonate (2×), brine (1×), dried over magnesium sulfate and concentrated under reduced pressure. The crude product was purified by flash chromatography (DCM/MeOH/NH$_4$OH=90/9/1) to give 9 g of the title intermediate as an oil (75% yield).
Analytical Data: MS m/z 512.8 (MH$^+$).

Step D—Preparation of 2-[(S)-1-(8-Methylaminooctyl)pyrrolidin-3-yl]-2,2-diphenylacetamide To a stirred solution of the intermediate from Step C (9 g, 17.6 mmol) in acetic acid (170 mL) under a nitrogen atmosphere was added palladium on carbon (10 wt. %, 600 mg) and palladium hydroxide on carbon (20 wt. %, wet, 600 mg). The reaction mixture was flushed with nitrogen three times and then placed under a hydrogen-containing balloon for 3 days at room temperature. The reaction mixture was filtered through Celite, washing with acetic acid, and the solvent was removed under reduced pressure. The resulting residue was purified by prep HPLC to afford 4.02 g of the title compound as its bis-trifluoroacetic acid salt, which as an oil (35% yield).
Analytical Data: MS m/z 422.2 (MH$^+$).
Alternatively, the title compound was prepared as follows:

Step A—Preparation of 8-(N-Benzyl-N-methylamino)octan-1-ol

From 8-Bromooctan-1-ol: To a 250 mL flask was charged N-benzyl-N-methylamine (24.3 g, 200 mmol), potassium carbonate (28 g, 200 mmol), 8-bromooctan-1-ol (14 g, 67 mmol) and acetonitrile (150 mL). This reaction mixture was stirred at 35-40° C. for 5 h. The solid material was then filtered and the filtrate was distilled to an oil under high vacuum to remove excess N-benzyl-N-methylamine. The residue was dissolved in 150 mL of MTBE and washed with 15% ammonium chloride solution (2×100 mL), brine (100 mL), dried with 20 g of sodium sulfate, filtered and distilled under vacuum to give 13.2 g of the title intermediate as an oil (79% yield).

From 8-Chlorooctan-1-ol: A 2-L flask was charged with benzylmethylamine (270 g, 2.23 mol), sodium carbonate (157 g, 1.48 mol), sodium iodide (11.1 g, 0.074 mol), 8-chlorooctanol (122 g, 0.74 mol) and acetonitrile (1000 mL) and the resulting suspension was stirred at 80° C. for 20-30 h. The reaction mixture was then concentrated to a volume of about 500 mL and water (600 mL) and tert-butyl methyl ether (1000 mL) were added. The MTBE layer was then separated and washed with water (500 mL). The MTBE solution was concentrated by distillation under vacuum to provide an oil and the oil was then further concentrated by distillation under high vacuum to remove excess benzylmethylamine. N-methyl-2-pyrrolidone (300 mL) was then added to the remaining oil and this solution concentrated by distillation under high vacuum to provide an oil. The oil was dissolved in MTBE (1000 mL) and the resulting solution was washed with water (2×500 mL), brine (500 mL), dried with sodium sulfate (100 g), filtered and concentrated by distillation to afford the title compound as an oil (178 g, 96% yield, >95% purity).

Step B—Preparation of Toluenesulfonic Acid 8-(N-Benzyl-N-methylamino)octan-1-yl Ester A 250 mL flask was charged with the intermediate from Step A (10 g), DABCO (6.72 g), and MTBE (100 ml). The reaction mixture was cooled to <10° C. and a solution of toluenesulfonic chloride (9.2 g) in 60 mL of MTBE was added at <15° C. This reaction mixture was stirred at room temperature for 2 h and then heptane (40 mL) was added and the mixture was filtered. The filtrate was distilled under vacuum to give 16 g of the title intermediate as an oil (99% yield).

Step C—Preparation of 2-f(S)-1-(8-N-Benzyl-N-methylaminooctyl)pyrrolidin-3-yl]-2,2-diphenylacetamide A 1000 mL flask with a nitrogen inlet was charged with the intermediate from Step B (16 g), 2,2-diphenyl-2-(S)-pyrrolidin-3-ylacetamide (10 g), diisopropylethylamine (10.3 g) and acetonitrile (200 mL). The reaction mixture was stirred at 45-50° C. for 20 h and then acetic anhydride (2 g) was added and the mixture stirred at room temperature for 2 hours. tert-Butyl methyl ether (300 mL) and water (400 mL) were added and the MTBE layer was separated and washed with water (2×150 mL) and then 1N HCl (1×150 mL). The aqueous layer was separated and washed with MTBE (3×100 mL) and then made basic with 27% ammonium hydroxide solution to pH>12. The basic aqueous layer was then extracted with MTBE (2×200 mL) and the MTBE layer was washed with water (200 mL), brine (200 mL), dried over sodium sulfate (20 g), filtered and distilled to give 16.5 g of the title intermediate as an oil (90% yield). If desired, this reaction can be conducted in N-methylpyrrolidone as the solvent. Additionally, potassium carbonate or sodium carbonate can be used in place of diisopropylethylamine and optionally sodium iodide may be added to the reaction mixture.

Step D—Preparation of 2-[(S)-1-(8-Methylaminooctyl)pyrrolidin-3-yl]-2,2-diphenylacetamide A 250 mL flask was charged with the intermediate from Step C (24 g), palladium on carbon (10% palladium on carbon with 50% water, 5.3 g)), isopropanol (160 mL) and 3 M HCl solution (30 mL). The reaction mixture was degassed with nitrogen and then was hydrogenated (45-50 psi) at room temperature for 16 h. The mixture was then filtered though a Celite pad and the filtrate was distilled to a volume of about 50 mL. The residue was dissolved in 1 N HCl (100 mL) and washed with dichloromethane (2×100 mL). The aqueous layer was adjusted to pH>12 by adding ammonium hydroxide and then extracted using MTBE (2×150 mL). The MTBE solution was then washed with water (100 mL), brine (100 mL), dried over sodium sulfate (30 g), filtered and distilled to oil which was dried under high vacuum to give 16.5 g of the title compound (91% yield).

Alternatively, the title compound was prepared as follows:

Step A—Preparation of 8,8-Dimethoxyoctanal

A 1 L flask was charged cyclooctene (50 g), methanol (250 mL) and dichloromethane (250 mL). Ozone was bubbled into the solution at −70° C. for 8 h. Toluenesulfonic acid (3 g) was then added and the reaction mixture was stirred at −70° C. for 6 h. Sodium bicarbonate (20 g) was then added and the reaction mixture stirred for an additional 2 h at −60° C. Finally, dimethyl sulfite (56 g) was added at −60° C. and the reaction mixture was stirred at room temperature for 16 h. The solid that had formed was filtered and filtrate was evaporated to oil. The oil was dissolved in dichloromethane (300 mL) and washed with 1% sodium bicarbonate solution (2×150 mL). The dichloromethane solution was then dried over sodium sulfate (50 g), filtered and distilled to give 60.3 g of the title intermediate as an oil (71% yield).

Step B—Preparation of 2-[(S)-1-(8-Oxooctyl)pyrrolidin-3-yl]-2,2-diphenylacetamide A 100 mL flask was charged with 2,2-diphenyl-2-(S)-pyrrolidin-3-ylacetamide (2.8 g), 8,8-dimethoxyoctanal (2.1 g), and dichloromethane (20 mL) and this mixture was stirred at room temperature for 1 h. Sodium triacetoxyborohydride (3.18 g) was added and the reaction mixture was stirred at room temperature for 14 h. A solution of 5% sodium bicarbonate (350 mL) was then added and this mixture stirred for 0.5 hours. The layers were separated and the aqueous layer was extracted with dichloromethane (20 mL). The combined dichloromethane solution was concentrated to a volume of about 20 mL, filtered through a silica gel pad (10 g) and washed with 10% methanol in dichloromethane (100 mL). The product solution was concentrated to an oil and the oil was dissolved in 50 mL of acetonitrile and stirred with 1% HCl (30 mL) for 16 hours. The mixture was made basic to approximately pH>12 by adding 28% ammonium hydroxide solution and then extracted with MTBE (2×100 mL). The MTBE layer was washed with brine (100 mL), dried over sodium sulfate (10 g), filtered and concentrated under vacuum to give 3.8 g of the title intermediate as an oil (93% yield).

Step C—Preparation of 2-[(S)-1-(8-N-Benzyl-N-methylaminooctyl)pyrrolidin-3-yl]-2,2-diphenylacetamide A 100 mL flask with a nitrogen inlet was charged with the intermediate from Step B (3 g), N-benzyl-N-methylamine (2.1 g) and dichloromethane (20 mL) and this mixture was stirred at room temperature for 1 h. Sodium triacetoxyborohydride (3.18 g) was added and the reaction mixture was stirred at room temperature for 14 h. The reaction was then quenched by adding 50 mL of 5% HCl and the resulting mixture was stirred for 0.5 hours. The layers were separated and the aqueous layer was washed with dichloromethane (20 mL). The aqueous layer was adjusted to pH>13 by adding 50% potassium hydroxide and extracted with MTBE (2×100 mL). The combined MTBE solution was washed with brine (100 ml), dried with sodium sulfate (10 g), filtered and concentrated to give 2.8 g of the title intermediate as an oil (75% yield). Using the procedure described in Step D above, this intermediate was converted into the title compound.

Alternatively, the title compound was prepared as the naphthalene-1,5-disulfonic acid salt using the following procedure:

Step A—Preparation of 8-(N-tert-Butoxycarbonyl-N-methylamino)octan-1-ol

A 1-L flask was charged with 8-(benzylmethylamino)octan-1-ol (49 g, 0.20 mol), isopropanol (400 mL), 2 N aqueous hydrochloric acid (100 mL) and activated carbon (5 g, DARCO) and the resulting mixture was stirred for 30 minutes. The mixture was then filtered to remove the activated carbon and to the filtrate was added palladium on carbon (5 g, 10% dry weight). The resulting mixture was degassed three times with nitrogen and then twice with hydrogen; and then the mixture was hydrogenated on a Parr shaker at 20-30 psi hydrogen for 12-24 hours. The mixture was then filtered through a 20 g pad of Celite and concentrated by distillation to a volume of about 100 mL. Isopropanol (200 mL) was added and this solution was again concentrated by distillation under vacuum to a volume of about 100 mL. This procedure was repeated two more times to give a solution containing 8-methylaminooctan-1-ol hydrochloride.

A 1-L flask was charged with the 8-methylaminooctanol hydrochloride isopropanol solution from above and triethylamine (30.3 g, 0.30 mol), and to this mixture was added di-tert-butyl dicarbonate (48 g, 0.22 mol) in portions. The resulting mixture was stirred at room temperature for 2-5 h and then the mixture was concentrated to a volume of about 300 mL. Water (200 mL) and ethyl acetate (400 mL) were added and this mixture was stirred for 15 minutes. The organic layer was then separated and washed with water (300 mL), brine (300 mL), dried over $Na_2SO_4$ (50 g), filtered and solvent reduced under vacuum to afford the title compound as a light yellow oil. (40 g, 77% yield, ~95% purity).

Step B—Preparation of Toluene-4-sulfonic Acid 8-(N-tert-Butoxycarbonyl-N-methylamino)octyl Ester In a 250 mL flask, a solution of the product from Step A (5.2 g, 20 mmol) and DABCO (3.13 g, 2.8 mmol) in MTBE (30 mL) was cooled to about 10° C. and a solution of p-toluenesulfonyl chloride (4.2 g, 22 mmol) in MTBE (20 mL) was added while maintaining the temperature of the reaction mixture at 20° C. or less. The resulting solution was then stirred at room temperature for 2 h. Water (100 mL) was added and the mixture was stirred for 15 minutes. The organic layer was separated, washed with water (100 mL), brine (100 mL) and then concentrated by distillation to give the title compound as an oil.

Step C—Preparation of 2-{(S)-1-[8-(N-tert-Butoxycarbonyl-N-methylamino)octylpyrrolidin-3-yl}-2,2-diphenylacetamide To a 500 mL flask was added the product from Step B (17.68 g, 43 mmol), the product from Preparation 1 (12 g, 43 mmol), diisopropylethylamine (16.55 g, 128 mmol) and acetonitrile (100 mL). The resulting mixture was stirred at 60° C. to 65° C. for 5 to 7 hours and then cooled to room temperature. The solvent was reduced in vacuo and isopropyl acetate (100 mL) was added to dissolve the residue. The resulting solution was washed with water (100 mL), saturated $NaHCO_3$ solution (100 mL), brine (100 mL), dried over $MgSO_4$ (5 g) and filtered to afford an orange solution.

A silica gel (115 g, 280-400 mesh) pad was pre-treated with 400 mL of isopropyl acetate containing 1% triethylamine, following by 250 mL of isopropyl acetate (the silica gel pad is about 6.4 cm in diameter and about 10.2 cm in height). The filtrate from above (about 150 mL in volume) was loaded directly onto the pre-treated silica pad and eluted with isopropyl acetate (400 mL) and then with 20% isopropanol in isopropyl acetate (1000 mL). The product fractions were combined and concentrated to afford the title compound as an oil (17.16 g, 77% yield, 97% purity).

Step D—Preparation of 2-[(S)-1-(8-Methylaminooctyl)pyrrolidin-3-yl]-2,2-diphenylacetamide Naphthalene-1,5-disulfonic Acid Salt To a 1000 mL flask was added the product from Step C (9.88 g, 19 mmol), 1,5-naphthalenedisulfonic acid tetrahydrate (13.69 g, 38 mmol) and isopropanol containing 3% water (497 mL). This mixture was heated to 85° C. for 3 to 5 hours, then slowly cooled to room temperature over a 4 hour period and then stirred at room temperature for 12 to 24 hours. The resulting solid was filtered and washed with isopropanol containing 3% water by volume (400 mL) and dried under vacuum for 10 to 15 hours at room temperature to give the title compound as a crystalline solid (12.59 g, 95% yield, ~99% purity).

If desired, this salt can be further purified by the following procedure:

To an 1 L flask was added 2-[(S)-1-(8-methylaminooctyl) pyrrolidin-3-yl]-2,2-diphenylacetamide naphthalene-1,5-disulfonic acid salt (21.4 g, 30.1 mmol) and isopropanol containing 3% water by volume (637 mL). The resulting slurry was stirred at 80° C. for 2 hours and then slowly cooled to room temperature and then stirred at room temperature for 12 hours. The resulting crystalline salt was filtered, washed with isopropanol (600 mL) and then dried under vacuum and nitrogen for 16 hours at room temperature to give the title compound as a white, crystalline solid (20.4 g, 96% yield).

Example 2

Synthesis of 2-[(S)-1-(8-Isopropylaminooctyl)pyrrolidin-3-yl]-2,2-diphenylacetamide Step A—Preparation of 2-[(S)-1-(8-Hydroxyoctyl) pyrrolidin-3-yl]-2,2-diphenylacetamide 8-Bromo-1-octanol (2.51 g, 12 mmol) in acetonitrile (10 mL) was added to a stirred solution of 2,2-diphenyl-2-(S)-pyrrolidin-3-ylacetamide (2.8 g, 10 mmol) and triethylamine (4.27 mL, 30 mmol) in acetonitrile (90 mL) at 40° C. The reaction mixture was heated at 55° C. for 16 h and then cooled to ambient temperature. The solvent was then removed under reduced pressure. The crude residue was dissolved in ethyl acetate (100 mL) and the organic phase was washed with saturated aqueous sodium bicarbonate (50 mL), dried over magnesium sulfate, filtered and concentrated under reduced pressure. The crude product was purified by flash chromatography (eluent: DCM/MeOH/NH$_4$OH=90/9/1) to give 1.8 g of the title intermediate as oil (44% yield).

Step B—Preparation of 2-[(S)-1-(8-Oxooctyl)pyrrolidin-3-yl]-2,2-diphenylacetamide Dimethylsulfoxide (1.57 mL, 22.1 mmol), followed by diisopropylethylamine (3.85 mL, 22.1 mmol) was added to a stirred solution of the intermediate from Step A (1.8 g, 4.4 mmol) in dichloromethane (44 mL) at 0° C. The reaction mixture was stirred at −10° C. for 15 min and then sulfur trioxide pyridine complex (2.1 g, 13.2 mmol) was added. The reaction mixture was stirred for a further 2 h at −10° C. Water (50 mL) and DCM (50 ml) were added and the organic layer was separated and washed with saturated aqueous sodium bicarbonate (2×30 mL), saturated aqueous copper (II) sulfate solution (2×15 mL) and brine (30 mL). The organic layer was then dried over magnesium sulfate and concentrated under reduced pressure to afford 1.5 g of the title intermediate as oil (84% yield).

Step C—Preparation of 2-[(S)-1-(8-Isopropylaminooctyl)pyrrolidin-3-yl]-2,2-diphenylacetamide The intermediate from Step B (40.6 mg, 0.1 mmol) and isopropylamine (10.2 μL, 0.12 mmol) in 1,2-dichloroethane (1 mL) were stirred at room temperature for 1 h and then sodium triacetoxyborohydride (35.1 mg, 1.5 mmol) was added. The reaction mixture was stirred for 16 h and then the solvent was removed under reduced pressure. The residue was purified by HPLC to afford the title compound as its bis-trifluoroacetic acid salt.

Analytical Data: MS m/z 450.3 (MH$^+$).

Using the procedures described herein and the appropriate starting materials, the compounds shown in Table IV were prepared:

TABLE IV

| Ex. | Compound | MS[1] |
| --- | --- | --- |
| 3 | 2-[(S)-1-(8-Prop-1-ylaminooctyl)pyrrolidin-3-yl]-2,2-diphenylacetamide | 450.2 |
| 4 | 2-[(S)-1-(8-Cyclopropylaminooctyl)pyrrolidin-3-yl]-2,2-diphenylacetamide | 448.3 |
| 5 | 2-[(S)-1-(8-Cyclobutylaminooctyl)pyrrolidin-3-yl]-2,2-diphenylacetamide | 462.2 |
| 6 | 2-[(S)-1-(8-Cyclopentylaminooctyl)pyrrolidin-3-yl]-2,2-diphenylacetamide | 476.3 |
| 7 | 2-[(S)-1-(8-Ethylaminooctyl)pyrrolidin-3-yl]-2,2-diphenylacetamide | 436.2 |
| 8 | 2-{(S)-1-[8-(2-Hydroxyethyl)aminooctyl]pyrrolidin-3-yl}-2,2-diphenylacetamide | 452.2 |
| 9 | 2-{(S)-1-[8-(R)-(1-Hydroxyprop-2-yl)aminooctyl]pyrrolidin-3-yl}-2,2-diphenylacetamide | 466.3 |
| 10 | 2-{(S)-1-[8-(1-Hydroxyprop-2-yl)aminooctyl]pyrrolidin-3-yl}-2,2-diphenylacetamide | 466.3 |
| 11 | 2-{(S)-1-[8-(S)-(1-Hydroxyprop-2-yl)aminooctyl]pyrrolidin-3-yl}-2,2-diphenylacetamide | 466.2 |
| 12 | 2-{(S)-1-[8-(2,2,2-Trifluoroethyl)aminooctyl]pyrrolidin-3-yl}-2,2-diphenylacetamide | 490.2 |
| 13 | 2-[(S)-1-(8-Benzylaminooctyl)pyrrolidin-3-yl]-2,2-diphenylacetamide | 498.2 |
| 14 | 2-[(S)-1-(9-Methylaminnonyl)pyrrolidin-3-yl]-2,2-diphenylacetamide | NA[‡] |
| 27 | 2-[(R)-1-(8-Methylaminooctyl)pyrrolidin-3-yl]-2,2-diphenylacetamide | 422.4 |

[1]Mass Spectrometry: m/z (MH$^+$).
[‡]Not available.

Additionally, using the procedures described herein and the appropriate starting materials, the compounds in Table V can be prepared:

TABLE V

| Ex. | Compound |
| --- | --- |
| 15 | 2-[(S)-1-(9-Isopropylaminononyl)pyrrolidin-3-yl]-2,2-diphenylacetamide |
| 16 | 2-[(S)-1-(9-Prop-1-ylaminononyl)pyrrolidin-3-yl]-2,2-diphenylacetamide |
| 17 | 2-[(S)-1-(9-Cyclopropylaminononyl)pyrrolidin-3-yl]-2,2-diphenylacetamide |

TABLE V-continued

| Ex. | Compound |
|---|---|
| 18 | 2-[(S)-1-(9-Cyclobutylaminononyl)pyrrolidin-3-yl]-2,2-diphenylacetamide |
| 19 | 2-[(S)-1-(9-Cyclopentylaminononyl)pyrrolidin-3-yl]-2,2-diphenylacetamide |
| 20 | 2-[(S)-1-(9-Ethylaminononyl)pyrrolidin-3-yl]-2,2-diphenylacetamide |
| 21 | 2-{(S)-1-[9-(2-Hydroxyethyl)aminononyl]pyrrolidin-3-yl}-2,2-diphenylacetamide |
| 22 | 2-{(S)-1-[9-(R)-(1-Hydroxyprop-2-yl)aminononyl]pyrrolidin-3-yl}-2,2-diphenylacetamide |
| 23 | 2-{(S)-1-[9-(1-Hydroxyprop-2-yl)aminononyl]pyrrolidin-3-yl}-2,2-diphenylacetamide |
| 24 | 2-{(S)-1-[9-(S)-(1-Hydroxyprop-2-yl)aminononyl]pyrrolidin-3-yl}-2,2-diphenylacetamide |
| 25 | 2-{(S)-1-[9-(2,2,2-Trifluoroethyl)aminononyl]pyrrolidin-3-yl}-2,2-diphenylacetamide |
| 26 | 2-[(S)-1-(9-Benzylaminononyl)pyrrolidin-3-yl]-2,2-diphenylacetamide |
| 28 | 2-[(R)-1-(8-Isopropylaminooctyl)pyrrolidin-3-yl]-2,2-diphenylacetamide |
| 29 | 2-[(R)-1-(8-Prop-1-ylaminooctyl)pyrrolidin-3-yl]-2,2-diphenylacetamide |
| 30 | 2-[(R)-1-(8-Cyclopropylaminooctyl)pyrrolidin-3-yl]-2,2-diphenylacetamide |
| 31 | 2-[(R)-1-(8-Cyclobutylaminooctyl)pyrrolidin-3-yl]-2,2-diphenylacetamide |
| 32 | 2-[(R)-1-(8-Cyclopentylaminooctyl)pyrrolidin-3-yl]-2,2-diphenylacetamide |
| 33 | 2-[(R)-1-(8-Ethylaminooctyl)pyrrolidin-3-yl]-2,2-diphenylacetamide |
| 34 | 2-{(R)-1-[8-(2-Hydroxyethyl)aminooctyl]pyrrolidin-3-yl}-2,2-diphenylacetamide |
| 35 | 2-{(R)-1-[8-(R)-(1-Hydroxyprop-2-yl)aminooctyl]pyrrolidin-3-yl}-2,2-diphenylacetamide |
| 36 | 2-{(R)-1-[8-(1-Hydroxyprop-2-yl)aminooctyl]pyrrolidin-3-yl}-2,2-diphenylacetamide |
| 37 | 2-{(R)-1-[8-(S)-(1-Hydroxyprop-2-yl)aminooctyl]pyrrolidin-3-yl}-2,2-diphenylacetamide |
| 38 | 2-{(R)-1-[8-(2,2,2-Trifluoroethyl)aminooctyl]pyrrolidin-3-yl}-2,2-diphenylacetamide |
| 39 | 2-[(R)-1-(8-Benzylaminooctyl)pyrrolidin-3-yl]-2,2-diphenylacetamide |
| 40 | 2-[(R)-1-(9-Methylaminononyl)pyrrolidin-3-yl]-2,2-diphenylacetamide |
| 41 | 2-[(R)-1-(9-Isopropylaminononyl)pyrrolidin-3-yl]-2,2-diphenylacetamide |
| 42 | 2-[(R)-1-(9-Prop-1-ylaminononyl)pyrrolidin-3-yl]-2,2-diphenylacetamide |
| 43 | 2-[(R)-1-(9-Cyclopropylaminononyl)pyrrolidin-3-yl]-2,2-diphenylacetamide |
| 44 | 2-[(R)-1-(9-Cyclobutylaminononyl)pyrrolidin-3-yl]-2,2-diphenylacetamide |
| 45 | 2-[(R)-1-(9-Cyclopentylaminononyl)pyrrolidin-3-yl]-2,2-diphenylacetamide |
| 46 | 2-[(R)-1-(9-Ethylaminononyl)pyrrolidin-3-yl]-2,2-diphenylacetamide |
| 47 | 2-{(R)-1-[9-(2-Hydroxyethyl)aminononyl]pyrrolidin-3-yl}-2,2-diphenylacetamide |
| 48 | 2-{(R)-1-[9-(R)-(1-Hydroxyprop-2-yl)aminononyl]pyrrolidin-3-yl}-2,2-diphenylacetamide |
| 49 | 2-{(R)-1-[9-(1-Hydroxyprop-2-yl)aminononyl]pyrrolidin-3-yl}-2,2-diphenylacetamide |
| 50 | 2-{(R)-1-[9-(S)-(1-Hydroxyprop-2-yl)aminononyl]pyrrolidin-3-yl}-2,2-diphenylacetamide |
| 51 | 2-{(R)-1-[9-(2,2,2-Trifluoroethyl)aminononyl]pyrrolidin-3-yl}-2,2-diphenylacetamide |
| 52 | 2-[(R)-1-(9-Benzylaminononyl)pyrrolidin-3-yl]-2,2-diphenylacetamide |
| 53 | 2-[1-(8-Methylaminooctyl)pyrrolidin-3-yl]-2,2-diphenylacetamide |
| 54 | 2-[1-(8-Isopropylaminooctyl)piperidin-4-yl]-2,2-diphenylacetamide |
| 55 | 2-[1-(8-Prop-1-ylaminooctyl)piperidin-4-yl]-2,2-diphenylacetamide |
| 56 | 2-[1-(8-Cyclopropylaminooctyl)piperidin-4-yl]-2,2-diphenylacetamide |
| 57 | 2-[1-(8-Cyclobutylaminooctyl)piperidin-4-yl]-2,2-diphenylacetamide |
| 58 | 2-[1-(8-Cyclopentylaminooctyl)piperidin-4-yl]-2,2-diphenylacetamide |
| 59 | 2-[1-(8-Ethylaminooctyl)piperidin-4-yl]-2,2-diphenylacetamide |
| 60 | 2-{1-[8-(2-Hydroxyethyl)aminooctyl]piperidin-4-yl}-2,2-diphenylacetamide |
| 61 | 2-{1-[8-(R)-(1-Hydroxyprop-2-yl)aminooctyl]piperidin-4-yl}-2,2-diphenylacetamide |
| 62 | 2-{1-[8-(1-Hydroxyprop-2-yl)aminooctyl]piperidin-4-yl}-2,2-diphenylacetamide |
| 63 | 2-{1-[8-(S)-(1-Hydroxyprop-2-yl)aminooctyl]piperidin-4-yl}-2,2-diphenylacetamide |
| 64 | 2-{1-[8-(2,2,2-Trifluoroethyl)aminooctyl]piperidin-4-yl}-2,2-diphenylacetamide |
| 65 | 2-[1-(8-Benzylaminooctyl)piperidin-4-yl]-2,2-diphenylacetamide |
| 66 | 2-[1-(9-Methylaminononyl)piperidin-4-yl]-2,2-diphenylacetamide |
| 67 | 2-[1-(9-Isopropylaminononyl)piperidin-4-yl]-2,2-diphenylacetamide |
| 68 | 2-[1-(9-Prop-1-ylaminononyl)piperidin-4-yl]-2,2-diphenylacetamide |
| 69 | 2-[1-(9-Cyclopropylaminononyl)piperidin-4-yl]-2,2-diphenylacetamide |
| 70 | 2-[1-(9-Cyclobutylaminononyl)piperidin-4-yl]-2,2-diphenylacetamide |
| 71 | 2-[1-(9-Cyclopentylaminononyl)piperidin-4-yl]-2,2-diphenylacetamide |
| 72 | 2-[1-(9-Ethylaminononyl)piperidin-4-yl]-2,2-diphenylacetamide |
| 73 | 2-{1-[9-(2-Hydroxyethyl)aminononyl]piperidin-4-yl}-2,2-diphenylacetamide |
| 74 | 2-{1-[9-(R)-(1-Hydroxyprop-2-yl)aminononyl]piperidin-4-yl}-2,2-diphenylacetamide |
| 75 | 2-{1-[9-(1-Hydroxyprop-2-yl)aminononyl]piperidin-4-yl}-2,2-diphenylacetamide |
| 76 | 2-{1-[9-(S)-(1-Hydroxyprop-2-yl)aminononyl]piperidin-4-yl}-2,2-diphenylacetamide |
| 77 | 2-{1-[9-(2,2,2-Trifluoroethyl)aminononyl]piperidin-4-yl}-2,2-diphenylacetamide |
| 78 | 2-[1-(9-Benzylaminononyl)piperidin-4-yl]-2,2-diphenylacetamide |

Comparative Example A

Synthesis of 2-[(S)-1-(8-Dimethylaminooctyl)pyrrolidin-3-yl]-2,2-diphenylacetamide A 50 mL dry round bottom flask was charged with 2,2-diphenyl-2-(S)-pyrrolidin-3-ylacetamide (200 mg, 0.714 mmol) and chloroform (20 mL), and then purged with nitrogen. Dimethylamine (535 μL, 1.071 mmol) was added followed by the dropwise addition of 1,8-dibromooctane (131 μL, 0.714 mmol). The reaction mixture was heated to 50° C. and stirred for approximately 60 hours. The yellow homogeneous mixture was cooled to room temperature and extracted with 1.0 M aqueous hydrogen chloride that was then washed with fresh chloroform. To the acidic aqueous layer was added ethyl acetate and the mixture was made basic to pH 13 with 10.0 M aqueous sodium hydroxide. The basic aqueous layer was then extracted with additional ethyl acetate (2×15 mL). The combined organic layers were then washed with saturated aqueous sodium chloride, dried over sodium sulfate, filtered and evaporated to give the crude product. The crude product (223.0 mg) was purified by preparatory HPLC and lyophilized to give the title compound as its bis(trifluoroacetate) salt, which was a white hygroscopic solid.

Analytical Data: MS m/z 436.4 $(C_{28}H_{41}N_3O+H)^+$; calc'd 436.3.

Comparative Example B

Synthesis of 2-[(S)-1-(9-Dimethylaminononyl)pyrrolidin-3-yl]-2,2-diphenylacetamide Using the procedures described herein and the appropriate starting materials, the title compound was prepared as its bis(trifluoroacetate) salt, which was a white hygroscopic solid.

Analytical Data: MS m/z 450.4 $(C_{29}H_{43}N_3O+H)^+$; calc'd 450.3.

Comparative Example C

Synthesis of 2-{(S)-1-[8-N-(2-Hydroxyethyl)-N-methylaminononyl]pyrrolidin-3-yl}-2,2-diphenylacetamide Using the procedures described herein and the appropriate starting materials, the title compound was prepared as its bis(trifluoroacetate) salt, which was a white hygroscopic solid.

Analytical Data: MS m/z 480.2; calc'd 480.4.

Comparative Example D

Synthesis of 2-[(S)-1-(8-Aminooctyl)pyrrolidin-3-yl]-2,2-diphenylacetamide

Step A—Preparation of 2-[(S)-1-(8-Bromoooctyl) pyrrolidin-3-yl]-2,2-diphenylacetamide To a solution of 2,2-diphenyl-2-(S)-pyrrolidin-3-ylacetamide (1.2 g, 0.004 mol) and diisopropylethylamine (0.74 mL, 0.004 mol) in a 1:1 (v/v) mixture of acetone and DMF (20 mL) was added 1,8 dibromooctane (0.99 mL, 0.005 mol). The mixture was heated to 40° C. for five hours and then concentrated to dryness and diluted with dichloromethane (20 mL). The resulting mixture was washed with saturated sodium bicarbonate (2×20 mL), brine (1×20 mL), dried over magnesium sulfate, filtered and concentrated. The residue was purified by silica gel chromatography, eluting with 5% methanol/dichloromethane, to provide 315 mg of the title intermediate as a white solid (15% yield).

Analytical Data: MS m/z 472.5 $(MH^+)$; calc'd 472.2.

Step B—Preparation of 2-[(S)-1-(8-Di-tert-BOC-aminooctyl)pyrrolidin-3-yl]-2,2-diphenylacetamide To a solution of di-tert-butyliminodicarboxylate (61 mg, 0.28 mmol) in 5 mL of DMF at −10° C. as added sodium hydride (11 mg, 0.28 mmol; 60% in mineral oil). The solution was allowed to slowly warm to room temperature and after stirring for 2 hours the intermediate from Step A (0.095 mg, 0.20 mol) in dimethyl formamide (5 mL) was added. The reaction mixture was then allowed to stir at room temperature overnight and then it was concentrated under vacuum, diluted with 10 mL of dichloromethane and this mixture was washed with saturated sodium bicarbonate (2×10 mL), brine (1×110 mL), dried over magnesium sulfate, filtered and concentrated to provide 120 mg of the title intermediate as a white solid. (99% yield).

Analytical Data: MS m/z 608.8 $(MH^+)$; calc'd 608.5.

Step C—Preparation of 2-[(S)-1-(8-Aminooctyl) pyrrolidin-3-yl]-2,2-diphenylacetamide To the intermediate from Step B (120 mg, 0.16 mmol) was added a mixture of trifluoroacetic acid (0.08 mL) in dichloromethane (0.720 mL) and the reaction mixture was stirred at room temperature for four hours. The reaction mixture was then concentrated to dryness under vacuum, diluted with dichloromethane (10 mL) and 1N sodium hydroxide was added slowly until pH reached 14. The organic layer as separated and washed with saturated sodium bicarbonate (2×10 mL), brine (1×110 mL), dried over magnesium sulfate, filtered, concentrated. The residue was purified by preparative HPLC to afford 27 mg of the title compound as its bis-trifluoroacetic acid salt, which was a white solid.

Analytical Data: MS m/z 408.6 $(MH^+)$; calc'd 408.3.

Assay 1

Radioligand Binding Assay

A. Membrane Preparation from Cells Expressing $hM_1$, $hM_2$, $hM_3$ and $hM_4$ Muscarinic Receptor Subtypes CHO (Chinese hamster ovary) cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS (Fetal Bovine Serum) and 250 µg/mL Geneticin. The cells were grown in a 5% $CO_2$, 37° C. incubator and lifted with 2 mm EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., 1951, *Journal of Biochemistry:* 193, 265. All membranes were stored frozen in aliquots at −80° C. or used immediately. Aliquots of prepared $hM_5$ receptor membranes were purchased directly from Perkin Elmer and stored at −80° C. until use.

B. Radioligand Binding Assay on Muscarinic Receptor Subtypes $hM_1$, $hM_2$, $hM_3$, $hM_4$ and $hM_5$ Radioligand binding assays were performed in 96-well microtiter plates in a total assay volume of 100 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$. The membranes were briefly homogenized using a Polytron tissue disrupter (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 µM in dilution buffer and then serially diluted 5× with dilution buffer to final concentrations ranging from 10 pM to 100 µM. The addition order and volumes to the assay plates were as follows: 25 µL radioligand, 25 µL diluted test compound, and 50 µL membranes. Assay plates were incubated for 60 minutes at 37° C. Binding reactions were terminated by rapid filtration over GF/B glass fiber filter plates (Perkin Elmer Inc., Wellesley, Mass.) pre-treated in 1% BSA. Filter plates were rinsed three times with wash buffer (10 mm HEPES) to remove unbound radioactivity. Plates were then air dried, and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23): 3099-108). $K_i$ values were converted to $pK_i$ values to determine the geometric mean and 95% confidence intervals. These summary statistics were then converted back to $K_i$ values for data reporting.

In this assay, a lower $K_i$ value indicates that a test compound has a higher binding affinity for the receptor tested. The compound of formula I was found to have a $K_i$ value of about 0.96 nM for the $M_3$ muscarinic receptor subtype in this assay.

Test compounds having a lower $K_i$ value in this assay have a higher binding affinity for the muscarinic receptor. The compounds of this invention which were tested in this assay had a $K_i$ value for $hM_2$ ranging from about 200 nM to less than 1 nM; typically ranging from about 100 nM to less than 1 nM; and a $K_i$ value for $hM_3$ ranging from about 100 nM to less than 1 nM; typically ranging from about 50 nM to less than 1 nM. For example, the compounds of Examples 1-11, 14, 26, 27, and 39 had a $K_i$ value for $hM_3$ of less than 50 nM. Thus, compounds of this invention were found to bind potently to the $hM_2$ and $hM_3$ receptor subtypes in this assay.

Additionally, the binding affinity for compounds of the formula:

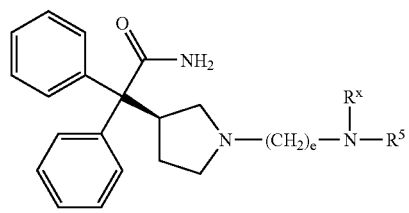

are shown in Table V (where $R^5$, $R^x$ and e are as defined in Table V):

TABLE V

| Compound Ex. No. | $R^5$ | $R^x$ | e | $hM_2$ (nM) | $\Delta^\dagger$ | $hM_3$ (nM) | $\Delta^\dagger$ |
|---|---|---|---|---|---|---|---|
| Ex. 1 | —CH$_3$ | —H | 8 | 3.8 | ×4.7 | 0.96 | ×2.6 |
| Comp. Ex. A | —CH$_3$ | —CH$_3$ | 8 | 18 | ×39 | 2.5 | ×52 |
| Comp. Ex. D | —H | —H | 8 | 150 | | 50 | |
| Ex. 14 | —CH$_3$ | —H | 9 | 1.7 | ×70 | 0.66 | ×37 |
| Comp. Ex. B | —CH$_3$ | —CH$_3$ | 9 | 120 | | 25 | |
| Ex. 8 | —CH$_2$CH$_2$OH | —H | 8 | 13 | ×6.3 | 5.1 | ×14 |
| Comp. Ex. C | —CH$_2$CH$_2$OH | —CH$_3$ | 8 | 83 | | 73 | |

$^\dagger$Change in binding affinity relative to compound of the invention.

The data in Table V demonstrate that substitution of the terminal amino group with an additional alkyl group, such as methyl, significantly decreases binding affinity at the $hM_2$ and $hM_3$ receptor subtypes. Additionally, the data in Table V demonstrate that removal of an alkyl group, such as methyl, from the terminal amino group significantly decreases binding affinity at the $hM_2$ and $hM_3$ receptor subtypes.

Assay 2

Muscarinic Receptor Functional Potency Assays

A. Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor.

cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells were rinsed once with dPBS and lifted with Trypsin-EDDA solution (0.05% trypsin/0.53 mm EDDA) as described in the Cell Culture and Membrane Preparation section above. The detached cells were washed twice by centrifugation at 650×g for five minutes in 5OmLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6 – 2.8 \times 10^6$ cells/mL.

The test compound was initially dissolved to a concentration of 400 µM in dilution buffer (dPBS supplemented with 1 mg/mL BSA (0.1%)), and then serially diluted with dilution buffer to final molar concentrations ranging from 100 µM to 0.1 nM. Oxotremorine was diluted in a similar manner.

To measure oxotremorine inhibition of adenylyl cyclase (AC) activity, 25 µL forskolin (25 µM final concentration diluted in dPBS), 25 µL diluted oxotremorine, and 50 µL cells were added to agonist assay wells. To measure the ability of a test compound to block oxotremorine-inhibited AC activity, 25 µL forskolin and oxotremorine (25 µM and 5 µM final concentrations, respectively, diluted in dPBS) 25 µL diluted test compound, and 50 µL cells were added to remaining assay wells.

Reactions were incubated for 10 minutes at 37° C. and stopped by addition of 100 µL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

In this assay, a lower $K_i$ value indicates that a test compound has a higher functional activity at the receptor tested. The compound of Example 1 was found to have a $K_i$ value of less than 5 nM for blockade of oxotremorine-inhibition of forskolin-mediated cAMP accumulation in CHO-K1 cells expressing the $hM_2$ receptor.

B. Blockade of Agonist-Mediated GTPγ[$^{35}$S] Binding

In a second functional assay, the functional potency of a test compound is determined by measuring the ability of the compound to block oxotremorine-stimulated [$^{35}$S]GTPγS binding in CHO-K1 cells expressing the $hM_2$ receptor. At the time of use, frozen membranes were thawed and then diluted in assay buffer with a final target tissue concentration of 5-10 µg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 µL of assay buffer with [$^{35}$S]GTPγS (0.4 nM), 25 µL of oxotremorine ($EC_{90}$) and GDP (3 uM), 25 µL of diluted test compound and 25 µL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 µL) was added to each well, and each plate was sealed and radioactivity counted on a topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that a test compound has a higher functional activity at the receptor tested. The compound of Example 1 was found to have a $K_i$ value of less than 5 nM for blockade of oxotremorine-stimulated [$^{35}$S]GTPγS binding in CHO-K1 cells expressing the $hM_2$ receptor.

C. Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency is determined by the ability of antagonists to inhibit agonist-mediated increases in intracellular calcium.

For FLIPR calcium stimulation assays, CHO cells stable expressing the $hM_1$, $hM_3$ and $cM_5$ receptors were seeded into 96-well FLIPR plates the night before the assay was done. Seeded cells were washed twice by Cellwash (MTX Labsystems, Inc.) with FLIPR buffer (10 mm HEPES, pH 7.4, 2 mm calcium chloride, 2.5 mm probenecid in Hank's Buffered Salt Solution (HBSS) without calcium and magnesium) to remove growth media and leave 50 µL/well of FLIPR buffer. The cells were then incubated with 50 µL/well of 4 µM FLUO-4AM (a 2× solution was made) for 40 minutes at 37° C., 5% carbon dioxide. Following the dye incubation period, cells were washed two times with FLIPR buffer, leaving a final volume of 50 µL/well.

To determine antagonist potency, the dose-dependent stimulation of intracellular $Ca^{2+}$ release for oxotremorine was first determined so that antagonist potency can later be measured against oxotremorine stimulation at an $EC_{90}$ concentration. Cells were first incubated with compound dilution buffer for 20 minutes, followed by agonist addition, which was performed by the FLIPR. An $EC_{90}$ value for oxotremorine was generated according to the method detailed in the FLIPR measurement and data reduction section below, in conjunction with the formula $ECF=((F/100-F)\textasciicircum 1/H)*EC_{50}$. An oxotremorine concentration of 3×ECF was prepared in stimulation plates such that an $EC_{90}$ concentration of oxotremorine was added to each well in the antagonist inhibition assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence was expressed as maximum fluorescence minus baseline fluorescence for each well. The raw data was analyzed against the logarithm of drug concentration by nonlinear regression with GraphPad Prism (GraphPad Software, Inc., San Diego, Calif.) using the built-in model for sigmoidal dose-response. Antagonist $K_i$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that a test compound has a higher functional activity at the receptor tested. The compound of formula I was found to have a $K_i$ value of less than 5 nM for blockade of agonist-mediated calcium release in CHO cells stable expressing the $hM_3$ receptor.

Assay 3

Determination of Duration of Bronchoprotection in Guinea Pig Model of Acetylcholine-Induced Bronchoconstriction This in vivo assay was used to assess the bronchoprotective effects of test compounds exhibiting muscarinic receptor antagonist activity.

Groups of six male guinea pigs (Duncan-Hartley (Hsd-Poc:DH) Harlan, Madison, Wis.) weighing between 250 and 350 g were individually identified by cage cards. Throughout the study animals were allowed access to food and water ad libitum.

The test compound was administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2=5\%$, $O_2=21\%$ and $N_2=74\%$) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre-and post-nebulization weights of the filled nebulizer.

The bronchoprotective effects of a test compound administered via inhalation were evaluated using whole body plethysmography at 1.5, 24, 48 and 72 hours post-dose.

Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-3 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of acetylcholine (Ach) (Sigma, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic mixture. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer progam enabled the collection and derivation of pulmonary values.

Starting this program initiated the experimental protocol and data collection. The changes in volume over time that occur within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach (Sigma-Aldrich, St. Louis, Mo.) (0.1 mg/mL) was infused intravenously for 1 minute from a syringe pump (sp21Oiw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second). Once the pulmonary function measurements were completed at minute 35 of this protocol, the guinea pig was removed from the plethysmograph and euthanized by carbon dioxide asphyxiation.

The data were evaluated in one or both of the following ways:

(a) Pulmonary resistance ($R_L$, cm $H_2O$/mL per second) was calculated from the ratio of "change in pressure" to "the change in flow."

The $R_L$ response to ACh (60 µg/min, IH) was computed for the vehicle and the test compound groups. The mean ACh response in vehicle-treated animals, at each pre-treatment time, was calculated and used to compute % inhibition of ACh response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective $ID_{50}$ (dose required to inhibit the ACh (60 µg/min) bronchoconstrictor response by 50%). The equation used was as follows:

$$Y=\text{Min}+(\text{Max}-\text{Min})/(1+10^{((\log ID50-X)*Hillslope)})$$

where X is the logarithm of dose, Y is the response (% Inhibition of ACh 20 induced increase in $R_L$). Y starts at Min and approaches asymptotically to Max with a sigmoidal shape.

(b) The quantity $PD_2$, which is defined as the amount of Ach or histamine needed to cause a doubling of the baseline pulmonary resistance, was calculated using the pulmonary resistance values derived from the flow and the pressure over a range of Ach or histamine challenges using the following equation (which is derived from an equation used to calculate $PC_{20}$ values described in American Thoracic Society. Guidelines for methacholine and exercise challenge testing—1999. *Am J Respir Crit Care Med.* 2000; 161:309-329):

$$PD_2 = \text{antilog}\left[\log C_1 + \frac{(\log C_2 - \log C_1)(2R_0 - R_1)}{R_2 - R_1}\right]$$

where:
$C_1$=concentration of Ach or histamine preceding $C_2$
$C_2$=concentration of Ach or histamine resulting in at least a 2-fold increase in pulmonary resistance ($R_L$)
$R_0$=Baseline $R_L$ value
$R_1$=$R_L$ value after $C_1$
$R_2$=$R_L$ value after $C_2$ An efficacious dose was defined as a dose that limited the bronchorestriction response to a 50 μg/mL dose of Ach to a doubling of the baseline pulmonary resistance ($PD_{2(50)}$).

Statistical analysis of the data was performed using a two-tailed Students t-test. A P-value <0.05 was considered significant.

Generally, a test compound having a $PD_{2(50)}$ less than about 200 μg/mL for ACh-induced bronchoconstriction at 1.5 hours post-dose in this assay is preferred. The compound of formula I was found to have a $PD_{2(50)}$ less than about 200 μg/mL for ACh-induced bronchoconstriction at 1.5 hours post-dose.

Assay 4

Inhalation Guinea Pig Salivation Assay

Guinea pigs (Charles River, Wilmington, Mass.) weighing 200-350 g were acclimated to the in-house guinea pig colony for at least 3 days following arrival. Test compound or vehicle were dosed via inhalation (IH) over a 10 minute time period in a pie shaped dosing chamber (R+S Molds, San Carlos, Calif.). Test solutions were dissolved in sterile water and delivered using a nebulizer filled with 5.0 mL of dosing solution. Guinea pigs were restrained in the inhalation chamber for 30 minutes. During this time, guinea pigs were restricted to an area of approximately 110 sq. cm. This space was adequate for the animals to turn freely, reposition themselves, and allow for grooming. Following 20 minutes of acclimation, guinea pigs were exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs were evaluated at 1.5, 6, 12, 24, 48, or 72 hrs after treatment.

Guinea pigs were anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals were placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) was inserted in the guinea pig's mouth. Five minutes later, the muscarinic agonist pilocarpine (3.0 mg/kg, s.c.) was administered and the gauze pad was immediately discarded and replaced by a new pre-weighed gauze pad. Saliva was collected for 10 minutes, at which point the gauze pad was weighed and the difference in weight recorded to determine the amount of accumulated saliva (in mg). The mean amount of saliva collected for animals receiving the vehicle and each dose of test compound was calculated. The vehicle group mean was considered to be 100% salivation. Results were calculated using result means (n=3 or greater). Confidence intervals (95%) were calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol,* 1996, 24:243-254.

The mean weight of saliva in vehicle-treated animals, at each pre-treatment time, was calculated and used to compute % inhibition of salivation, at the corresponding pre-treatment time, at each dose. The inhibition dose-response data were fitted to a a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used was as follows:

$$Y = Min + (Max-Min)/(1+10^{((\log ID50-X)*Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective ID50 was used to compute the apparent lung selectivity index of the test compound. Generally, compounds having an apparent lung selectivity index greater than about 5 are preferred. In this assay, the compound of formula I had an apparent lung-selectivity index greater than about 5.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g were used in these studies. Under isoflurane anesthesia (to effect), animals were instrumented with common carotid artery and jugular vein catheters (PE-50 tubing). The catheters were exteriorized utilizing a subcutaneous tunnel to the subscapular area. All surgical incisions were sutured with 4-0 Ethicon Silk and the catheters locked with heparin (1000 units/mL). Each animal was administered saline (3 mL, SC) at the end of surgery as well as buprenorphine (0.05 mg/kg, IM). Animals were allowed to recover on a heating pad before being returned to their holding rooms.

Approximately 18 to 20 hours following surgery, the animals were weighed and the carotid artery catheter on each animal was connected to a transducer for recording arterial pressure. Arterial pressure and heart rate was recorded using a Biopac MP-100 Acquisition System. Animals were allowed to acclimate and stabilize for a period of 20 minutes.

Each animal was challenged with methylcholine (MCh) (0.3 mg/kg, iv) administer through the jugular venous line and the cardiovascular response was monitored for 10 minutes. The animals were then placed into the whole body dosing chamber, which was connected to a nebulizer containing the test compound or vehicle solution. The solution was nebulized for 10 minutes using a gas mixture of breathable air and 5% carbon dioxide with a flow rate of 3 liters/minute. The animals were then removed from the whole body chamber and returned to their respective cages. At 1.5 and 24 h post-dosing, the animals were re-challenged with MCh (0.3 mg/kg, iv) and the hemodynamic response was determined. Thereafter, the animals were euthanized with sodium pentobarbital (150 mg/kg, IV).

MCh produces a decrease in mean arterial pressure (MAP) and decrease in heart rate (bradycardia). The peak decrease, from baseline, in MAP (depressor responses) was measured for each MCh challenge (before and after IH dosing). The bradycardic effects were not used for analysis since these responses were not robust and reproducible. The effects of treatment on the MCh responses are expressed as % inhibition (mean +/−SEM) of the control depressor responses. Two-way ANOVA with the appropriate post-hoc test was used to test the effects of treatment and pretreatment time. The depressor responses to MCh were relatively unchanged at 1.5 and 24 h after inhalation dosing with vehicle.

The ratio of the anti-depressor ID50 to bronchoprotective $ID_{50}$ was used to compute apparent lung-selectivity of the test compound. Generally, compounds having an apparent lung-selectivity index greater than 5 are preferred. In this assay, the compound of Example 1 had an apparent lung-selectivity index greater than 5.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A pharmaceutical composition comprising a pharmaceutically-acceptable carrier and a therapeutically effective amount of a compound having the formula:

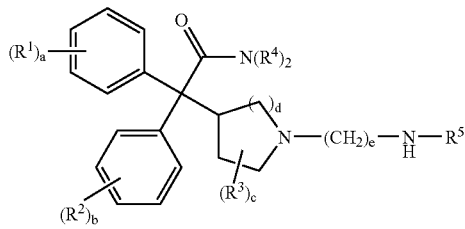

wherein: each $R^1$ and $R^2$ is independently selected from $C_{1-4}$ alkyl, $C_{2-4}$ alkenyl, $C_{2-4}$ alkynyl, $C_{3-6}$ cycloalkyl, cyano, halo —$OR^a$, —$SR^a$, —$S(O)R^a$, —$S(O)_2R^a$ and —$NR^bR^c$; or two adjacent $R^1$ groups or two adjacent $R^2$ groups are joined to form $C_{3-6}$ alkylene, —($C_{2-4}$ alkylene)-O— or —O—($C_{1-4}$ alkylene)-O—;

each $R^3$ is independently selected from $C_{1-4}$ alkyl and fluoro;

each $R^4$ is independently selected from hydrogen $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl, $C_{3-6}$ heterocyclic, —$CH_2$—$R^6$ and —$CH_2CH_2$—$R^7$; or both $R^4$ groups are joined together with the nitrogen atom to which they are attached to form $C_{3-6}$ heterocyclic;

$R^5$ is selected from $C_{1-6}$ alkyl, $C_{2-6}$ alkenyl, $C_{2-6}$ alkynyl, $C_{3-6}$ cycloalkyl, and —$CH_2$—$R^8$; wherein each alkyl, alkenyl, alkynyl and cycloalkyl group is optionally substituted with —OH or 1 to 3 fluoro substituents;

each $R^6$ is independently selected from $C_{3-6}$ cycloalkyl, $C_{6-10}$ aryl, $C_{2-9}$ heteroaryl and $C_{3-6}$ heterocyclic;

each $R^7$ is independently selected from $C_{3-6}$ cycloalkyl, $C_{6-10}$ aryl, $C_{2-9}$ heteroaryl, $C_{3-6}$ heterocyclic, —OH, —O($C_{1-6}$ alkyl), —O($C_{3-6}$ cycloalkyl), —O($C_{6-10}$ aryl), —($C_{2-9}$ heteroaryl), —S($C_{1-6}$ alkyl), —S(O)($C_{1-6}$ alkyl), —S(O)$_2$($C_{1-6}$ cycloalkyl), —S($C_{3-6}$ cycloalkyl), —S(O)($C_{3-6}$ cycloalkyl), —S(O)$_2$($C_{3-6}$ cycloalkyl), —S($C_{6-10}$ aryl), —S(O)($C_{6-10}$ aryl), —S(O)$_2$($C_{6-10}$ aryl), —S($C_{2-9}$ heteroaryl), —S(O)($C_{2-9}$ heteroaryl) and —S(O)$_2$($C_{2-9}$ heteroaryl);

each $R^8$ is independently selected from $C_{3-6}$ cycloalkyl, $C_{6-10}$ aryl, $C_{2-9}$ heteroaryl and $C_{3-6}$ heterocyclic;

each $R^a$ is independently selected from hydrogen, $C_{1-4}$ alkyl, $C_{2-4}$ alkenyl, $C_{2-4}$ alkynyl and $C_{3-6}$ cycloalkyl; each $R^b$ and $R^c$ is independently selected from hydrogen, $C_{1-4}$ alkyl, $C_{2-4}$ alkenyl, $C_{2-4}$ alkynyl and $C_{3-6}$ cycloalkyl; or $R^b$ and $R^c$ are joined together with the nitrogen atom to which they are attached to form $C_{3-6}$ heterocyclic;

a is an integer from 0 to 3; b is an integer from 0 to 3; c is an integer from 0 to 4; d is 1 or 2; e is 8 or 9;

wherein each alkyl, alkylene, alkenyl, alkynyl and cycloalkyl group in $R^1$, $R^2$, $R^3$, $R^4$, $R^7$, $R^a$, $R^b$ and $R^c$ is optionally substituted with 1 to 5 fluoro substituents; each aryl, cycloalkyl, heteroaryl and heterocyclic group in $R^1$, $R^2$, $R^4$, $R^5$, $R^6$, $R^7$, $R^8$, $R^a$, $R^b$ and $R^c$ is optionally substituted with 1 to 3 substituents independently selected from $C_{1-4}$ alkyl, $C_{2-4}$ alkenyl, $C_{2-4}$ alkynyl, cyano, halo, —O($C_{1-4}$ alkyl), —S($C_{1-4}$ alkyl), —S(O)($C_{1-4}$ alkyl), —S(O)$_2$($C_{1-4}$ alkyl), —$NH_2$, —NH($C_{1-4}$ alkyl) and —N($C_{1-4}$ alkyl)$_2$, wherein each alkyl, alkenyl and alkynyl group is optionally substituted with 1 to 5 fluoro substituents; and each —$CH_2$— group in —($CH_2$)$_e$— is optionally substituted with 1 or 2 substituents independently selected from $C_{1-2}$ alkyl, —OH and fluoro;

or a pharmaceutically-acceptable salt or solvate or stereoisomer thereof.

2. The pharmaceutical composition of claim 1, wherein $R^5$ is $C_{1-5}$ alkyl, wherein the alkyl group is optionally substituted with —OH or 1 to 3 fluoro substituents.

3. The pharmaceutical composition of claim 1, wherein $R^5$ is $C_{3-5}$ cycloalkyl, wherein the cycloalkyl group is optionally substituted with —OH or 1 to 3 fluoro substituents.

4. The pharmaceutical composition of claim 1, wherein $R^5$ is selected from:
(a) —$CH_2$—($C_{3-5}$ cycloalkyl), wherein the cycloalkyl group is optionally substituted with —OH or 1 to 3 fluoro substituents; and
(b) —$CH_2$-(phenyl), wherein the phenyl group is optionally substituted with 1 to 3 substituents independently selected from $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substituents.

5. The pharmaceutical composition of claim 1, wherein each $R^4$ is hydrogen.

6. The pharmaceutical composition of claim 1, wherein a, b and c are 0.

7. The pharmaceutical composition of claim 1, wherein d is 1.

8. The pharmaceutical composition of claim 1, wherein d is 2.

9. The pharmaceutical composition of claim 1, wherein e is 8.

10. The pharmaceutical composition of claim 1, wherein e is 9.

11. The pharmaceutical composition of claim 1, wherein the compound has the formula:

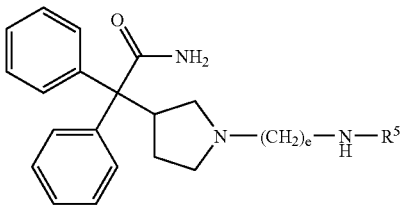

or a pharmaceutically-acceptable salt or solvate or stereoisomer thereof.

12. The pharmaceutical composition of claim 11, wherein the stereochemistry of the compound at the 3-position of the pyrrolidine ring is (S).

13. The pharmaceutical composition of claim 11, wherein the stereochemistry of the compound at the 3-position of the pyrrolidine ring is (R).

14. The pharmaceutical composition of claim 1, wherein the compound is selected from:

2-[(S)-1-(8-methylaminooctyl)pyrrolidin-3-yl]-2,2-diphenylacetamide;
2-[(S)-1-(8-isopropylaminooctyl)pyrrolidin-3-yl]-2,2-diphenylacetamide;
2-[(S)-1-(8-prop-1-ylaminooctyl)pyrrolidin-3-yl]-2,2-diphenylacetamide;
2-[(S)-1-(8-cyclopropylaminooctyl)pyrrolidin-3-yl]-2,2-diphenylacetamide;
2-[(S)-1-(8-cyclobutylaminooctyl)pyrrolidin-3-yl]-2,2-diphenylacetamide;
2-[(S)-1-(8-cyclopentylaminooctyl)pyrrolidin-3-yl]-2,2-diphenylacetamide;
2-[(S)-1-(8-ethylaminooctyl)pyrrolidin-3-yl]-2,2-diphenylacetamide;
2-{(S)-1-[8-(2-hydroxyethyl)aminooctyl]pyrrolidin-3-yl}-2,2-diphenylacetamide;
2-{(S)-1-[8-(R)-(1-hydroxyprop-2-yl)aminooctyl]pyrrolidin-3-yl}-2,2-diphenylacetamide;
2-{(S)-1-[8-(1-hydroxyprop-2-yl)aminooctyl]pyrrolidin-3-yl}-2,2-diphenylacetamide;
2-{(S)-1-[8-(S)-(1-hydroxyprop-2-yl)aminooctyl]pyrrolidin-3-yl}-2,2-diphenylacetamide;
2-{(S)-1-[8-(2,2,2-trifluoroethyl)aminooctyl]pyrrolidin-3-yl}-2,2-diphenylacetamide;
2-[(S)-1-(8-benzylaminooctyl)pyrrolidin-3-yl]-2,2-diphenylacetamide;
2-[(R)-1-(8-methylaminooctyl)pyrrolidin-3-yl]-2,2-diphenylacetamide;
2-[(R)-1-(8-isopropylaminooctyl)pyrrolidin-3-yl]-2,2-diphenylacetamide;
2-[(R)-1-(8-prop-1-ylaminooctyl)pyrrolidin-3-yl]-2,2-diphenylacetamide;
2-[(R)-1-(8-cyclopropylaminooctyl)pyrrolidin-3-yl]-2,2-diphenylacetamide;
2-[(R)-1-(8-cyclobutylaminooctyl)pyrrolidin-3-yl]-2,2-diphenylacetamide;
2-[(R)-1-(8-cyclopentylaminooctyl)pyrrolidin-3-yl]-2,2-diphenylacetamide;
2-[(R)-1-(8-ethylaminooctyl)pyrrolidin-3-yl]-2,2-diphenylacetamide;
2-{(R)-1-[8-(2-hydroxyethyl)aminooctyl]pyrrolidin-3-yl}-2,2-diphenylacetamide;
2-{(R)-1-[8-(R)-(1-hydroxyprop-2-yl)aminooctyl]pyrrolidin-3-yl}-2,2-diphenylacetamide;
2-{(R)-1-[8-(1-hydroxyprop-2-yl)aminooctyl]pyrrolidin-3-yl}-2,2-diphenylacetamide;
2-{(R)-1-[8-(S)-(1-hydroxyprop-2-yl)aminooctyl]pyrrolidin-3-yl}-2,2-diphenylacetamide;
2-{(R)-1-[8-(2,2,2-trifluoroethyl)aminooctyl]pyrrolidin-3-yl}-2,2-diphenylacetamide;
2-[(R)-1-(8-benzylaminooctyl)pyrrolidin-3-yl]-2,2-diphenylacetamide;
2-[(S)-1-(9-methylaminononyl)pyrrolidin-3-yl]-2,2-diphenylacetamide;
2-[(S)-1-(9-isopropylaminononyl)pyrrolidin-3-yl]-2,2-diphenylacetamide;
2-[(S)-1-(9-prop-1-ylaminononyl)pyrrolidin-3-yl]-2,2-diphenylacetamide;
2-[(S)-1-(9-cyclopropylaminononyl)pyrrolidin-3-yl]-2,2-diphenylacetamide;
2-[(S)-1-(9-cyclobutylaminononyl)pyrrolidin-3-yl]-2,2-diphenylacetamide;
2-[(S)-1-(9-cyclopentylaminononyl)pyrrolidin-3-yl]-2,2-diphenylacetamide;
2-[(S)-1-(9-ethylaminononyl)pyrrolidin-3-yl]-2,2-diphenylacetamide;
2-{(S)-1-[9-(2-hydroxyethyl)aminononyl]pyrrolidin-3-yl}-2,2-diphenylacetamide;
2-{(s)-1-[9-(R)-(1-hydroxyprop-2-yl)aminononyl]pyrrolidin-3-yl}-2,2-diphenylacetamide;
2-{(S)-1-[9-(1-hydroxyprop-2-yl)aminononyl]pyrrolidin-3-yl}-2,2-diphenylacetamide;
2-{(S)-1-[9-(S)-(1-hydroxyprop-2-yl)aminononyl]pyrrolidin-3-yl}-2,2-diphenylacetamide;
2-{(S)-1-[9-(2,2,2-trifluoroethyl)aminononyl]pyrrolidin-3-yl}-2,2-diphenylacetamide;
2-[(S)-1-(9-benzylaminononyl)pyrrolidin-3-yl]-2,2-diphenylacetamide;
2-[(R)-1-(9-methylaminononyl)pyrrolidin-3-yl]-2,2-diphenylacetamide;
2-[(R)-1-(9-isopropylaminononyl)pyrrolidin-3-yl]-2,2-diphenylacetamide;
2-[(R)-1-(9-prop-1-ylaminononyl)pyrrolidin-3-yl]-2,2-diphenylacetamide;
2-[(R)-1-(9-cyclopropylaminononyl)pyrrolidin-3-yl]-2,2-diphenylacetamide;
2-[(R)-1-(9-cyclobutylaminononyl)pyrrolidin-3-yl]-2,2-diphenylacetamide;
2-[(R)-1-(9-cyclopentylaminononyl)pyrrolidin-3-yl]-2,2-diphenylacetamide;
2-[(R)-1-(9-ethylaminononyl)pyrrolidin-3-yl]-2,2-diphenylacetamide;
2-{(R)-1-[9-(2-hydroxyethyl)aminononyl]pyrrolidin-3-yl}-2,2-diphenylacetamide;
2-{(R)-1-[9-(R)-(1-hydroxyprop-2-yl)aminononyl]pyrrolidin-3-yl}-2,2-diphenylacetamide;
2-{(R)-1-[9-(1-hydroxyprop-2-yl)aminononyl]pyrrolidin-3-yl}-2,2-diphenylacetamide;
2-{(R)-1-[9-(S)-(1-hydroxyprop-2-yl)aminononyl]pyrrolidin-3-yl}-2,2-diphenylacetamide;

2-{(R)-1-[9-(2,2,2-trifluoroethyl)aminononyl]pyrrolidin-3-yl}-2,2-diphenylacetamide;
2-[(R)-1-(9-benzylaminononyl)pyrrolidin-3-yl]-2,2-diphenylacetamide;
2-[1-(8-methylaminooctyl)pyrrolidin-3-yl]-2,2-diphenylacetamide;
2-[1-(8-isopropylaminooctyl)piperidin-4-yl]-2,2-diphenylacetamide;
2-[1-(8-prop-1-ylaminooctyl)piperidin-4-yl]-2,2-diphenylacetamide;
2-[1-(8-cyclopropylaminooctyl)piperidin-4-yl]-2,2-diphenylacetamide;
2-[1-(8-cyclobutylaminooctyl)piperidin-4-yl]-2,2-diphenylacetamide;
2-[1-(8-cyclopentylaminooctyl)piperidin-4-yl]-2,2-diphenylacetamide;
2-[1-(8-ethylaminooctyl)piperidin-4-yl]-2,2-diphenylacetamide;
2-{1-[8-(2-hydroxyethyl)aminooctyl]piperidin-4-yl}-2,2-diphenylacetamide;
2-{1-[8-(R)-(1-hydroxyprop-2-yl)aminooctyl]piperidin-4-yl}-2,2-diphenylacetamide;
2-{1-[8-(1-hydroxyprop-2-yl)aminooctyl]piperidin-4-yl}-2,2-diphenylacetamide;
2-{1-[8-(S)-(1-hydroxyprop-2-yl)aminooctyl]piperidin-4-yl}-2,2-diphenylacetamide;
2-{1-[8-(2,2,2-trifluoroethyl)aminooctyl]piperidin-4-yl}-2,2-diphenylacetamide;
2-[1-(8-benzylaminooctyl)piperidin-4-yl]-2,2-diphenylacetamide;
2-[1-(9-methylaminononyl)piperidin-4-yl]-2,2-diphenylacetamide;
2-[1-(9-isopropylaminononyl)piperidin-4-yl]-2,2-diphenylacetamide;
2-[1-(9-prop-1-ylaminononyl)piperidin-4-yl]-2,2-diphenylacetamide;
2-[1-(9-cyclopropylaminononyl)piperidin-4-yl]-2,2-diphenylacetamide;
2-[1-(9-cyclobutylaminononyl)piperidin-4-yl]-2,2-diphenylacetamide;
2-[1-(9-cyclopentylaminononyl)piperidin-4-yl]-2,2-diphenylacetamide;
2-[1-(9-ethylaminononyl)piperidin-4-yl]-2,2-diphenylacetamide;
2-{1-[9-(2-hydroxyethyl)aminononyl]piperidin-4-yl}-2,2-diphenylacetamide;
2-{1-[9-(R)-(1-hydroxyprop-2-yl)aminononyl]piperidin-4-yl}-2,2-diphenylacetamide;
2-{1-[9-(1-hydroxyprop-2-yl)aminononyl]piperidin-4-yl}-2,2-diphenylacetamide;
2-{1-[9-(S)-(1-hydroxyprop-2-yl)aminononyl]piperidin-4-yl}-2,2-diphenylacetamide;
2-{1-[9-(2,2,2-trifluoroethyl)aminononyl]piperidin-4-yl}-2,2-diphenylacetamide; and
2-[1-(9-benzylaminononyl)piperidin-4-yl]-2,2-diphenylacetamide;

and pharmaceutically-acceptable salts and solvates thereof.

15. The pharmaceutical composition of claim 1, which is suitable for administration by inhalation.

16. The pharmaceutical composition of claim 1, which further comprises a therapeutically effective amount of a $\beta_2$ adrenergic receptor agonist.

17. The pharmaceutical composition of claim 1, which further comprises a therapeutically effective amount of a steroidal anti-inflammatory agent.

18. The pharmaceutical composition of claim 1, which further comprises a therapeutically effective amount of a phosphodiesterase-4 inhibitor.

19. The pharmaceutical composition of claim 1, which further comprises a therapeutically effective amount of a $\beta_2$ adrenergic receptor agonist and a steroidal anti-inflammatory agent.

20. The pharmaceutical composition of claim 15, which is in the form of an aerosol.

21. The pharmaceutical composition of claim 15, which is in the form of a powder.

22. The pharmaceutical composition of claim 15, which is in the form of a solution.

23. The pharmaceutical composition of claim 15, wherein the compound is micronized.

24. The pharmaceutical composition of claim 23, wherein the compound is combined with the carrier to form a suspension.

25. The pharmaceutical composition of claim 24, wherein the carrier is an isotonic aqueous solution.

26. The pharmaceutical composition of claim 23, wherein the compound is combined with the carrier to form a free flowing powder.

27. The pharmaceutical composition of claim 26, wherein the carrier is lactose or starch.

28. The pharmaceutical composition of claim 15, which further comprises a liquefied propellant.

29. The pharmaceutical composition of claim 15, which is administered using a nebulizer inhaler.

30. The pharmaceutical composition of claim 15, which is administered using a metered-dose inhaler.

31. The pharmaceutical composition of claim 15, which is administered using a dry powder inhaler.

* * * * *

UNITED STATES PATENT AND TRADEMARK OFFICE
CERTIFICATE OF CORRECTION

PATENT NO.         : 7,351,717 B2                                            Page 1 of 1
APPLICATION NO. : 11/602703
DATED              : April 1, 2008
INVENTOR(S)       : Mammen et al.

It is certified that error appears in the above-identified patent and that said Letters Patent is hereby corrected as shown below:

Column 59
line 58, insert a --,-- after "halo".

Column 60
line 1, "ioined" should be --joined--.

line 13, "-($C_{2-9}$heteroaryl)" should be -- -O($C_{2-9}$heteroaryl)--.

line 14, "-S(O)$_2$($C_{1-6}$cycloalkyl)" should be -- -S(O)$_2$($C_{1-6}$alkyl)--.

Column 62
line 35, "2-{(s)-1-[9-(R)-(1-hydroxyprop-2-yl)" should be --2-{(S)-1-[9-(R)-(1-hydroxyprop-2-yl)--.

Signed and Sealed this

Thirtieth Day of September, 2008

JON W. DUDAS
*Director of the United States Patent and Trademark Office*